US009814485B2

(12) United States Patent
Pratt et al.

(10) Patent No.: US 9,814,485 B2
(45) Date of Patent: Nov. 14, 2017

(54) HYDRAULICALLY ACTUATED SKIN GRAFT HARVESTING

(71) Applicant: KCI Licensing, Inc., San Antonio, TX (US)

(72) Inventors: Benjamin A. Pratt, Poole Dorset (GB); Christopher Brian Locke, Bournemouth (GB); Timothy Mark Robinson, Basingstoke (GB); Kevin Higley, San Antonio, TX (US); Tab Randolph, San Antonio, TX (US); T. Blane Sanders, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 506 days.

(21) Appl. No.: 14/581,646

(22) Filed: Dec. 23, 2014

(65) Prior Publication Data
US 2015/0201954 A1 Jul. 23, 2015

Related U.S. Application Data

(60) Provisional application No. 61/922,511, filed on Dec. 31, 2013.

(51) Int. Cl.
*A61B 17/322* (2006.01)
*A61B 17/00* (2006.01)

(52) U.S. Cl.
CPC .. *A61B 17/322* (2013.01); *A61B 2017/00761* (2013.01); *A61B 2017/00774* (2013.01); *A61B 2017/3225* (2013.01)

(58) Field of Classification Search
CPC .......... A61B 17/322; A61B 2017/3225; A61B 2017/00761; A61B 2017/00774;
(Continued)

(56) References Cited

U.S. PATENT DOCUMENTS

2006/0258956 A1  11/2006  Haberstich et al.
2007/0255168 A1  11/2007  Hibner et al.
(Continued)

OTHER PUBLICATIONS

PCT Notification of Transmittal of the International Search Report and the Written Opinion of the International Searching Authority, or the Declaration, PCT/US2014/072188, dated Mar. 19, 2015 (12 sheets).
(Continued)

*Primary Examiner* — Sarah W Aleman
*Assistant Examiner* — Rachel S Highland
(74) *Attorney, Agent, or Firm* — Reza Mollaaghababa; Thomas J. Engellenner; Pepper Hamilton LLP

(57) ABSTRACT

The present invention generally relates to devices and systems that utilize an inflatable bladder for generating, cutting, capturing, and/or transplanting one or more skin blisters. In some aspects, methods and devices in accordance with the present teachings can enable the harvesting of skin grafts from an increased variety of potential donor sites, such as areas of the body having uneven surfaces or a smaller radius of curvature (e.g., the arm) or large area donor sites where the creation of a vacuum may require a high power negative pressure source. In various aspects, systems, devices, and methods in accordance with the present teachings can also enable the efficient transplant of the grafts directly from the skin graft harvester to the recipient site without the transfer of the grafts generated by the harvester to another substrate prior to transplantation.

70 Claims, 11 Drawing Sheets

(58) Field of Classification Search
CPC ....... A61B 2017/320044; A61B 2017/320048; A61B 17/320783; A61B 2017/320791
USPC .................................................. 606/131, 132
See application file for complete search history.

(56) References Cited

U.S. PATENT DOCUMENTS

| | | | |
|---|---|---|---|
| 2012/0035618 A1* | 2/2012 | Sabir ................... | A61B 17/322 606/132 |
| 2012/0271320 A1* | 10/2012 | Hall ................. | A61B 17/32053 606/132 |
| 2013/0145596 A1 | 6/2013 | Sabir et al. | |
| 2013/0204273 A1 | 8/2013 | Sabir et al. | |

OTHER PUBLICATIONS

Office Action dated Dec. 18, 2014 for U.S. Appl. No. 13/120,799.

* cited by examiner

HYDRAULICALLY ACTUATED SKIN GRAFT HARVESTING

CROSS-REFERENCE TO RELATED APPLICATION

This application claims priority to U.S. Provisional Application No. 61/922,511, filed Dec. 31, 2013. Prior application is incorporated herein by reference in its entirety.

FIELD OF THE INVENTION

The present invention relates generally to devices and methods for generating and harvesting skin grafts.

BACKGROUND

Skin is the largest organ of the human body, representing approximately 16% of a person's total body weight. Because it interfaces with the environment, skin has an important function in body defense, acting as an anatomical barrier from pathogens and other environmental substances. Skin also provides a semi-permeable barrier that prevents excessive fluid loss while ensuring that essential nutrients are not washed out of the body. Other functions of skin include insulation, temperature regulation, and sensation. Skin tissue may be subject to many forms of damage, including burns, trauma, disease, and depigmentation (e.g., vitiligo).

Skin grafts are often used to repair such skin damage. Skin grafting is a surgical procedure in which a section of skin is removed from one area of a person's body (autograft), removed from another human source (allograft), or removed from another animal (xenograft), and transplanted to a recipient site of a patient, such as a wound site. Typically it is preferable to use an autograft instead of an allograft or a xenograft to reduce complications, such as graft failure and rejection of the skin graft.

A problem encountered when using an autograft is that skin is taken from another area of a person's body to produce the graft, resulting in trauma and wound generation at the donor site. Generally, the size of the graft matches the size of the recipient site, and thus a large recipient site requires removal of a large section of skin from a donor site, leading to increased pain and discomfort and longer healing time. Additionally, as the size of the section of skin removed from the donor site increases, so does the possibility of infection.

Techniques have been developed for harvesting a large number of smaller grafts, e.g., so-called micrografts, to reduce the trauma at the donor site. By removing only a fraction of the skin at a donor site and leaving regions of healthy skin surrounding the excised regions, a large amount of skin for transplantation can be obtained with less discomfort. Micrograft harvesting can also reduce the healing time and risk of infection at the donor site.

Suction blistering, for example, is a technique for harvesting micrografts that utilizes a source of negative pressure in conjunction with heat to facilitate blister formation. Though this technique can be effective to generate micrografts, suction blistering typically requires a gas-tight seal to be formed between the blister raising device and the skin surface to enable the application of negative pressure.

SUMMARY

Methods and devices disclosed herein can generate skin grafts without necessarily requiring a negative pressure source and/or the creation of a gas-tight seal between the harvester and the skin. As a result, methods and devices in accordance with the present teachings can enable the harvesting of skin grafts from an increased variety of potential donor sites, such as areas of the body having uneven surfaces or a smaller radius of curvature (e.g., the inner arm). Moreover, methods and devices in accordance with various aspects of the present teachings can enable the efficient transfer of the graft directly from the harvester to the recipient site without requiring transfer to an intermediate substrate.

In one embodiment, a device for obtaining a skin graft is disclosed that includes an inflatable bladder defining at least one fluid-receiving chamber and a cutting assembly that can be disposed between the bladder and the skin surface at a donor site. The cutting assembly includes a base plate, which has a plurality of holes permitting portions of the skin to contact the bladder when the base plate is disposed on the skin surface and the bladder is disposed above the cutting assembly. The inflatable bladder couples to the cutting assembly and adheres to the exposed skin regions such that inflation of the bladder is effective to deform the bladder's shape and draw the adherent portions of the skin through the holes in the base plate. In some aspects, the cutting assembly also includes a cutter plate disposed between the base plate and the bladder for cleaving the portions of the skin extending through the holes in the base plate, for example, following inflation of the bladder and blister formation. In various aspects, the inflatable bladder includes non-inflatable and/or rigid portions such that when the inflatable bladder is coupled to the cutting assembly, the non-inflatable and/or rigid portions are registered with the plurality of holes in the base plate. In this manner, the non-inflatable portions are contacted with the skin at the donor site through the holes, and can be coupled thereto via an adhesive, for example, disposed on a surface of the inflatable bladder. Because the non-inflatable and/or rigid portions of the bladder may not expand, inflation of the bladder thereby raises these portions (and thus the skin to which they are coupled) relative to the base plate.

As will be discussed in detail below, systems incorporating such devices can additionally include, for example, a fluid source fluidly coupled to the chamber for inflation of the bladder and/or one or more additional blister raising mechanisms. By way of example, devices in accordance with the present teachings can be used in conjunction with heat and/or suction blistering techniques to further promote the formation of blisters through the plurality of holes in the base plate.

In some embodiments, a device for obtaining a skin graft is disclosed that includes an inflatable bladder having an upper layer and a lower layer defining a chamber therebetween for receiving an inflation fluid. When compressed against the skin, the lower layer of the inflatable bladder can be pressed into contact with portions of the patient's skin at the donor site through a plurality of holes in a base plate of a cutting assembly disposed between the bladder and the skin. Following inflation of the bladder and blister formation (e.g., after the skin is raised via the application of heat, suction, or both), a cutter plate disposed between the base plate and the bladder can cleave the blisters. In some aspects, inflation of the bladder raises relative to the base plate the portion of the lower layer having skin coupled thereto. Indeed, in some aspects, inflation of the bladder itself can be effective to pull the skin through the holes and/or raise blisters.

In systems in accordance with the present teachings, a fluid source can be fluidly coupled to the chamber of the inflatable bladder for delivering fluid to the chamber (or withdrawing fluid therefrom). It will be appreciated in light of the present teachings that the chamber can be coupled to the fluid source via any known fluid coupling elements and one or more delivery mechanisms (e.g., pump). By way of non-limiting example, the inflatable chamber can include one or more ports for coupling the chamber to a conduit that is coupled to the fluid source. The fluid for inflating the chamber can be a liquid or a gas, for example, though in some embodiments, the fluid can be a heated liquid that aids in blister formation.

The inflatable bladder can have a variety of configurations and can be composed from a variety of materials. For example, in some aspects, the upper and lower layers of the inflatable bladder can comprise a polymeric material. By way of non-limiting example, the inflatable bladder can be made of two sheets of polymeric membrane that are sealed together to define the fluid receiving chamber of the bladder therebetween. The sheets need not be of the same material, and indeed, can be selected so as to selectively promote movement of the bladder upon inflation. By way of example, the upper layer can be stiffer than the lower layer such that the lower layer preferentially expands in response to a given fluid pressure within the chamber (e.g., so as to promote the raising of portions of the lower layer relative to the base plate). In some aspects, selected locations at the upper and lower layers can be coupled to one another (e.g., spot welded) such that the upper and lower layers at these locations do not separate from one another upon inflation of the chamber. That is, a distance between the upper and lower layers of the inflatable bladder can remain substantially constant during inflation of the bladder at these coupled locations, though adjacent to these locations the layers separate as the chamber is filled with fluid. Thus, in various aspects, when the coupled locations (e.g., non-inflatable portions) are aligned with the plurality of holes in the base plate and the bladder is inflated, the inflated portions surrounding the non-inflatable locations expand against the base plate such that the non-inflatable portions (e.g., having skin coupled thereto) are raised relative to the base plate.

Optionally, the device can include a heating element that can heat the skin at the donor site to promote the formation of blisters. For example, a heating element (e.g., an EMR or light source or resistive heating element such as a nichrome wire) can be disposed in a head that can be removably attached to the cutting assembly and inflatable bladder for heating of the skin. When the heating element is a light source, for example, the layers of the inflatable bladder can comprise a translucent polymer to allow the light to be delivered therethrough to the skin at the donor site. Though it will be appreciated in light of the present teachings that blisters can be raised without the application of negative pressure, in some embodiments one or more locations at which the upper and lower layers of the inflatable bladder are coupled can include a channel extending through the upper and lower layers to enable a negative pressure to be applied to the skin through the channel (e.g., to promote suction blister formation and/or to help maintain the skin in secure contact with the bladder).

In various aspects, the cutting assembly can have a variety of configurations but is generally configured to be disposed between the bladder and the skin surface. In some embodiments, the cutting assembly (and bladder) can be flexible to allow the device to conform to the donor site when the bladder is compressed against the donor site. In some aspects, the cutting assembly can be removably coupled to the lower layer of the bladder (e.g., via an adhesive). For example, in addition to the base plate and cutter plate, the cutting assembly can include a top plate disposed between the cutter plate and the lower layer of the inflatable bladder that can be reversibly coupled to the lower layer via a UV- or heat-reversible adhesive. Like the base plate, the top plate can define one or more holes extending therethrough that can be aligned with the plurality of holes in the base plate. Likewise, the cutter plate can also have a plurality of holes extending therethrough that can be initially aligned with the holes in the base plate and the top plate in a first position. Once the blisters have been raised (e.g., through the aligned holes in the base, cutter, and top plates), the cutter plate can be actuated relative to the base plate to disrupt the alignment of the holes, thereby cleaving the blisters from the donor site.

In some embodiments, a method for generating a skin graft is disclosed that includes applying a cutting assembly to a donor site of a patient's skin, the cutting assembly having a base plate with a plurality of holes extending therethrough. An inflatable bladder can be coupled to portions of the patient's skin at the donor site through the plurality of holes and then inflated during and/or after heating the skin to raise blisters through the plurality of holes in the base plate. After blister formation, the cutting assembly can be actuated to cleave the blisters from the donor site. By way of example, a cutter plate disposed between the base plate and the inflatable bladder can be moved relative to the base plate so as to disrupt the alignment of the plurality of holes in the base plate with one or more holes in the cutter plate.

In some aspects, the cutting assembly can be coupled to the inflatable bladder prior to applying the cutting assembly to the donor site. By way of example, an adhesive can be disposed on a lower layer of the inflatable bladder such that the cutting assembly can be adhered thereto (e.g., prior to applying the cutting assembly to the skin) In some aspects, the inflatable bladder having the cutting assembly coupled thereto is compressed against the skin such that portions of the skin can be coupled (e.g., adhered) to the lower layer of the bladder through holes in the cutting assembly.

In some aspects, after cleaving the blisters from the donor site, the inflatable bladder can be deflated and/or removed from the donor site with the cleaved blisters remaining coupled (e.g., adhered) thereto. The cutting assembly can be removed (e.g., peeled) from the inflatable bladder) and the inflatable bladder having the plurality of cleaved blisters coupled thereto can be applied to a donor site. In some aspects, an adhesive for coupling the blisters to the inflatable bladder and/or the cutting assembly can be a UV- or heat-deactivated adhesive, such that the adhesive can be deactivated, for example, after applying the inflatable bladder to the recipient site to allow for detachment of the blisters.

These and other aspects of the devices of the invention are described in the figures, description and claims that follow. While various features have been individually described, such features are not mutually exclusive of each other. Any combination of design features disclosed herein can be integrated into the devices of the invention.

BRIEF DESCRIPTION OF THE DRAWINGS

FIG. 5A is a side cross-sectional view of an inflatable bladder and cutting assembly according to the invention. FIG. 5B is a side cross-sectional view of an inflatable bladder and cutting assembly placed on a donor site; FIG. 5C is a side cross-sectional view like FIG. 5B, showing the bladder in its inflated state; FIG. 5D is a side cross-sectional view of an inflatable bladder and cutting assembly, showing cleavage of skin blisters; FIG. 5E is a side cross-sectional view of an inflatable bladder showing cleaved blisters adhering to the bladder; and FIG. 5F is a side cross-sectional view showing removal of the inflatable bladder and following attachment of skin grafts at a treatment site;

DETAILED DESCRIPTION

Figure 1:
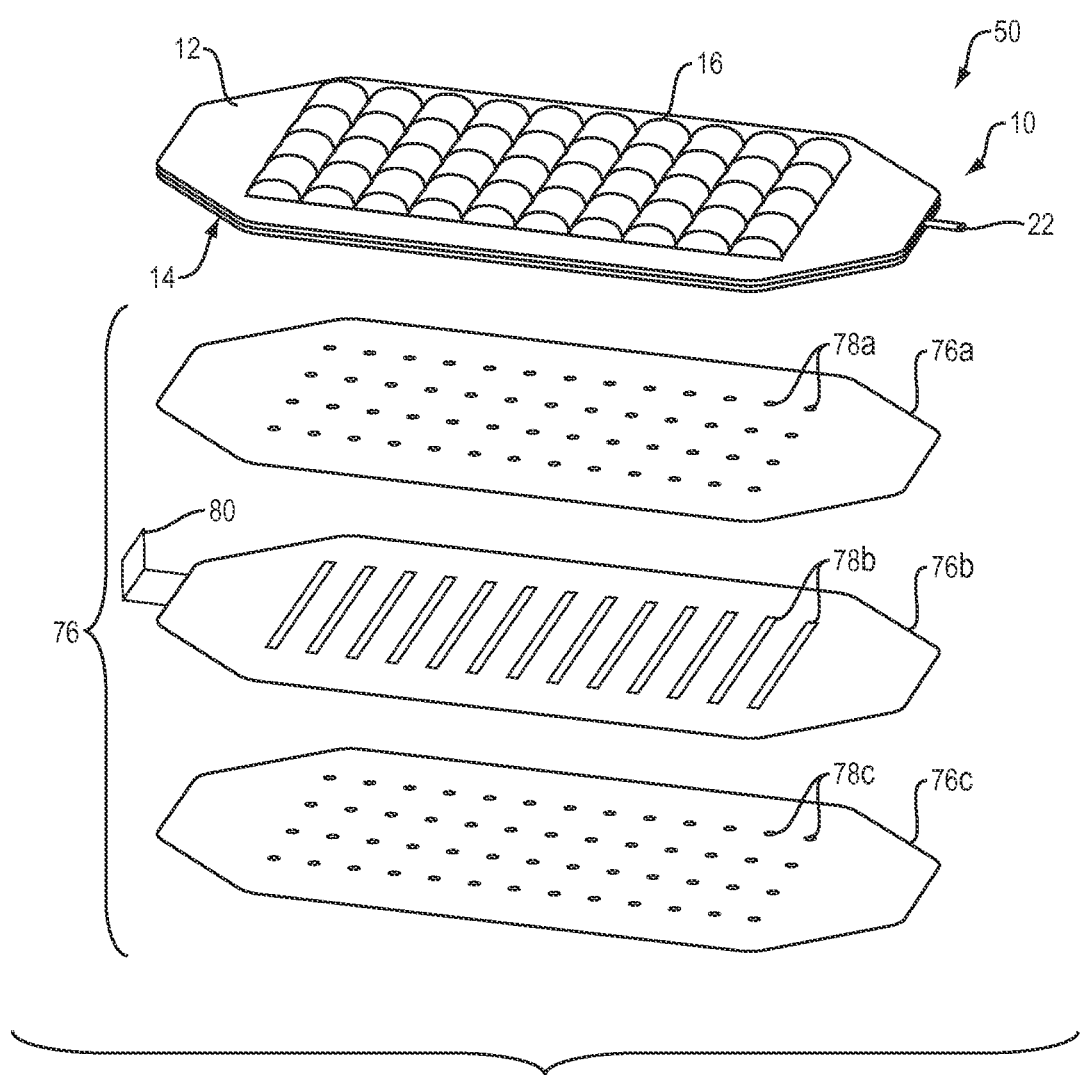
FIG. 1 is a schematic exploded view of an exemplary skin blister harvesting device according to various aspects of the present teachings.

In the following detailed description of non-limiting, illustrative embodiments, reference is made to the accompanying drawings that form a part hereof. Other embodiments may be utilized and logical, structural, mechanical, electrical, and chemical changes may be made without departing from the scope of this specification. To avoid detail not necessary to enable those skilled in the art to practice the embodiments described herein, the description may omit certain information known to those skilled in the art. The following detailed description is not to be taken in a limiting sense, with the scope of the illustrative embodiments being defined by the appended claims.

The term "micrograft" as used herein is intended to encompass skin grafts that have a width or length less than a millimeter, more preferably, less than 100 microns. A micrograft is an excised skin segment having at least one dimension parallel to the skin surface that is less than a millimeter, preferably less than 100 micrometers, more preferably in some applications less than 10 micrometers. The minimum width or length is preferably less than 500 micrometers, preferably less than 100 micrometers or less than 50 micrometers or less than 10 micrometers or less than 1 micrometer. For example, a micrograft can be generally circular, oval or oblong in a plane parallel to the skin surface and have a diameter or major axis that ranges from about 1 millimeter to 0.01 micrometers, or from about 100 micrometers to about 0.1 micrometers, or more preferably from about 50 to 1 micrometers. Micrografts also typically have a depth dimension that extends at least through the epidermis and preferably in some applications encompasses at least one layer of basal cells. The depth can range from about 500 micrometers to about 0.1 micrometers, preferably from about 100 micrometers to about 1 micrometer.

The term "harvesting" as used herein is intended to encompass the removal of one or more skin grafts from a skin graft generating device, as well as the transplantation of such skin grafts and any intermediate steps, such as culturing, expanding, stretching, treating or otherwise preparing a skin graft for transfer to a recipient site.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. For instance, a concentration value of about 30% can mean a concentration between 27% and 33%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The present invention generally relates to devices and systems that utilize an inflatable bladder for generating, cutting, capturing, and/or transplanting one or more skin blisters. Skin blister harvesters in accordance with various aspects of the present teachings can generate skin grafts without requiring a negative pressure source and/or the creation of a gas-tight seal between the harvester and the skin. As such, methods and devices in accordance with the present teachings can enable the harvesting of skin grafts from an increased variety of potential donor sites, such as areas of the body having uneven surfaces or a smaller radius of curvature (e.g., the arm) or large area donor sites where the creation of a vacuum may require a high power negative pressure source. In various aspects, systems, devices, and methods in accordance with the present teachings can also enable the efficient transplant of the grafts directly from the skin graft harvester to the recipient site without the transfer of the grafts generated by the harvester to another substrate (e.g., Tegaderm™) prior to transplantation.

Figure 2A:
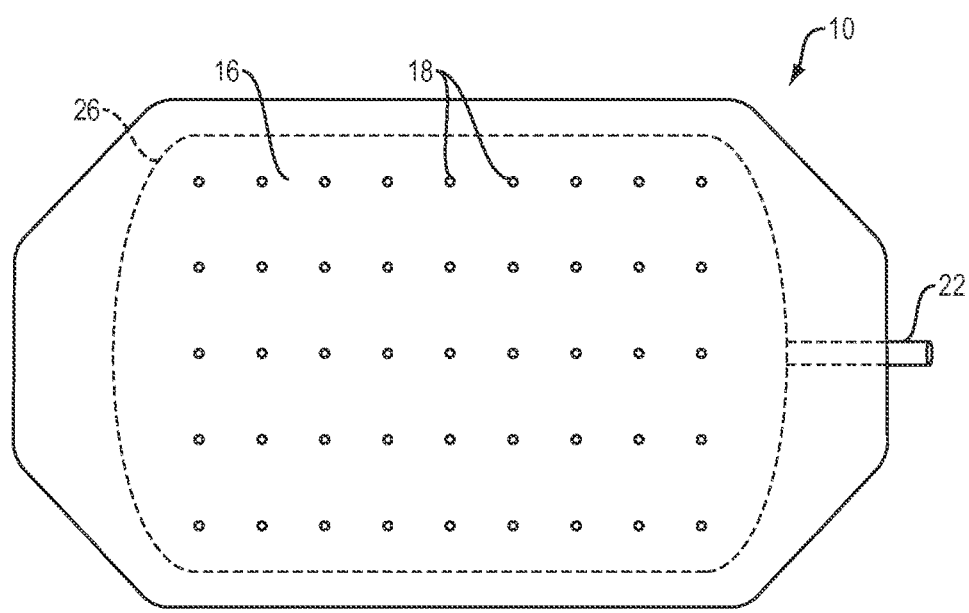
FIG. 2A is schematic top view of the skin blister harvesting device of FIG. 1.
Figure 2B:
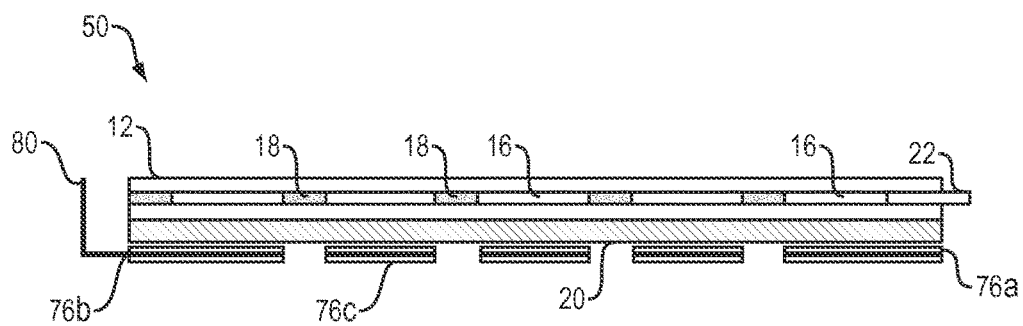
FIG. 2B is a cross-sectional view of the skin blister harvesting device of FIG. 1 when the bladder is not inflated.
Figure 2C:
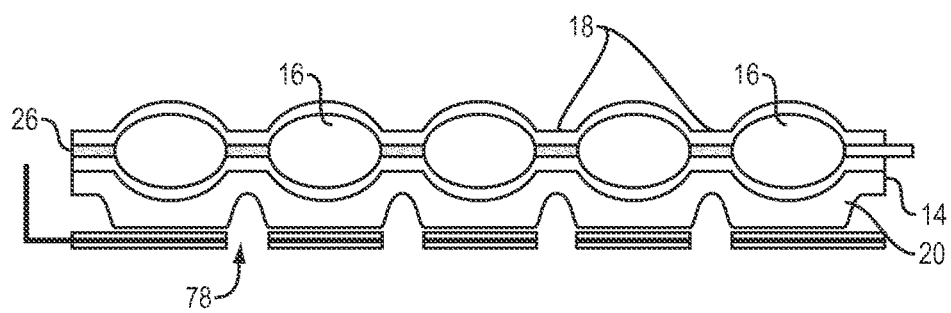
FIG. 2C is a cross-sectional view of the skin blister harvesting device of FIG. 1 when the bladder is inflated.
Figure 3:
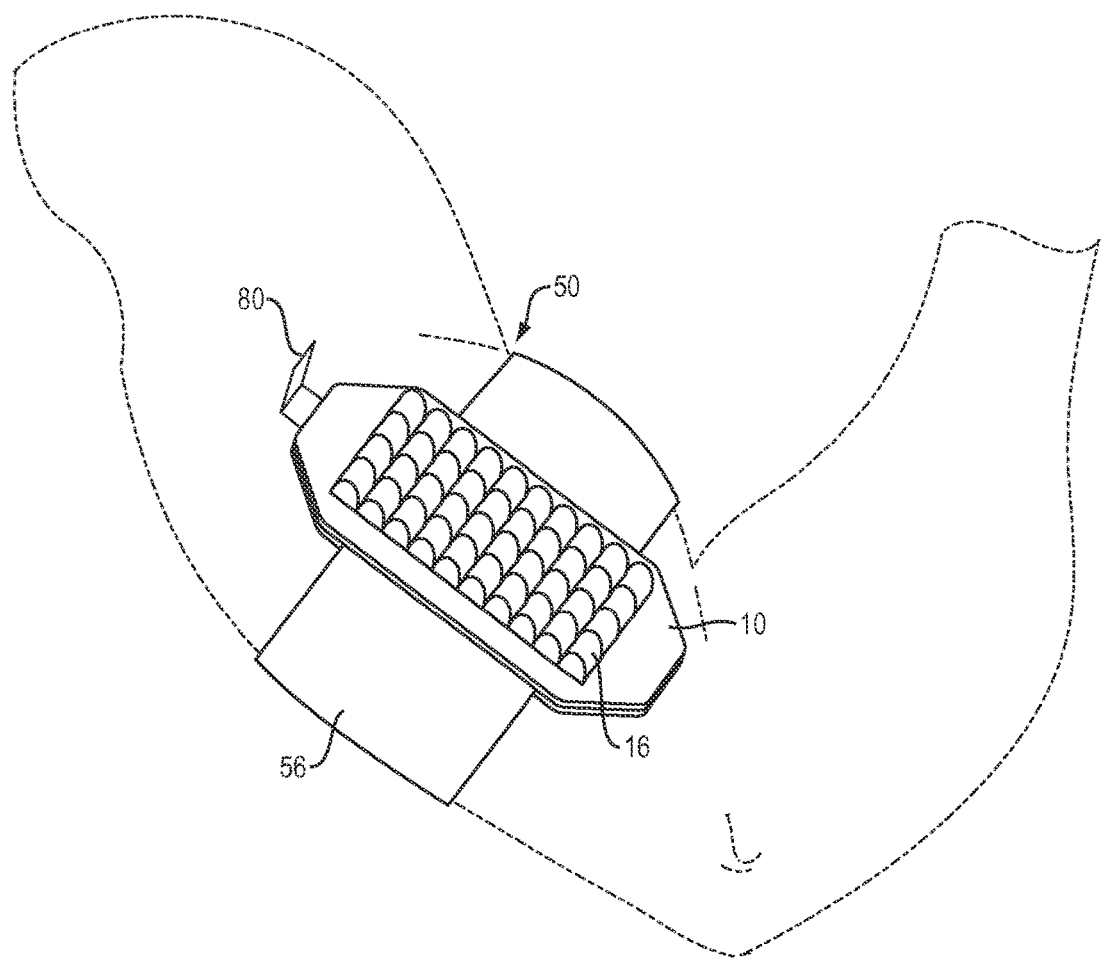
FIG. 3 is a schematic of the skin blister harvesting device of FIG. 1 applied to a donor site of a patient's arm.

With reference now to FIGS. 1-3, an exemplary skin graft harvester 50 in accordance with various aspects of the present teachings is depicted. As shown in the exploded view of FIG. 1, the exemplary skin graft harvester 50 generally includes an inflatable bladder 10 and a cutting assembly 76 that can be disposed between the bladder 10 and the patient's skin. For example, as depicted in FIG. 3, the skin graft harvester can be compressed and/or secured in place at a donor site where skin grafts are to be obtained (e.g., on the arm) with a strap 56, which can be coupled to the inflatable bladder 10 or the cutting assembly 76. The exemplary cutting assembly 76 includes one or more holes 78a-c for receiving a portion of the patient's skin when the cutting assembly 76 is disposed on the skin surface. As will be discussed in detail below, the bladder 10 can be coupled to the cutting assembly 76 such that inflation of the bladder 10 is effective to raise portions of the skin through the holes 78a-c in the cutting assembly 76. After raising the skin blister(s) through the one or more holes, the cutting assembly 76 can be actuated to cleave the portions of the skin extending through the cutting assembly 76.

The inflatable bladder 10 can have a variety of configurations but generally includes one or more fluid receiving chambers such that the bladder 10 inflates when fluid is received within the chamber. For example, as best shown in FIGS. 2A-2C, the exemplary bladder 10 includes an upper layer 12 and a lower layer 14 that can be joined (e.g., sealed) together at the periphery 26 (shown in phantom in FIG. 2A) so as to define a chamber 16 between the upper and lower layers 12, 14. A fluid port 22 in fluid communication with the chamber 16 can extend from the inflatable bladder 10 for delivery of an inflation fluid to the sealed chamber 16. Thus, as the chamber 16 is filled with inflation fluid, at least a portion of the bladder 10 can expand (e.g., change shape). By way of example, portions of the upper and/or lower layers 12, 14 can comprise a stretchable or flexible material such that the delivery of inflation fluid into the chamber 16 under pressure is effective to stretch those portions of the bladder 10. Additionally or alternatively, the upper and/or lower layers 12, 14 can comprise sufficient material such that the layers are slack when the bladder is un-inflated, but become taut upon an increase in the volume and/or pressure of the chamber 16.

Moreover, the bladder 10 can be configured such that portions thereof are differentially expanded (e.g., some portions expand differently or do not substantially expand) upon inflation of the bladder 10. By way of example, in an unexpanded state, the lower layer 14 may contain greater amounts of "slack" relative to the upper layer 12 such that the lower layer 14 can expand more relative to the upper layer 12 upon inflation of the bladder. Alternatively or additionally, various portions of the bladder 10 can be made of materials having different characteristics such that a given fluid pressure within the fluid chamber differentially affects the expansion of various portions of the bladder. By way of example, the lower layer 14 can be made of a stiffer (e.g., less flexible) material than the upper layer 12 such that the lower layer 14 tends to stretch more for a given fluid pressure within the chamber 16.

In various aspects, some portions of the bladder 10 may be non-inflatable or sufficiently rigid such that these portions do not substantially expand (e.g., change shape) upon inflation of the bladder 10. By way of example, various locations of the upper layer 12 and the lower layer 14 of the bladder 10 can be coupled to one another such that the upper and lower layers 12, 14 do not separate from one another at these locations upon inflation of the chamber 16. As shown in FIG. 2A, for example, the upper and lower layers 12, 14 can be coupled (e.g., sealed, spot-welded) at a number of separated locations 18 (e.g., in an array). Thus, as the fluid-receiving chamber 16 is inflated, the upper and lower layers 12, 14 between the locations 18 bulge out, thereby resulting in the exemplary surface contour of the bladder 10 best shown in FIGS. 1 and 2C. As will be discussed in detail below, the lower layer 14 of the bladder 10 can be coupled to the cutting assembly 76 and to portions of the skin extending therethrough such that this differential expansion of the bladder 10 (e.g., bulging out of portions of the bladder) selectively moves portions of the bladder 10 having skin coupled thereto relative to the cutting assembly 76.

Figure 4A:
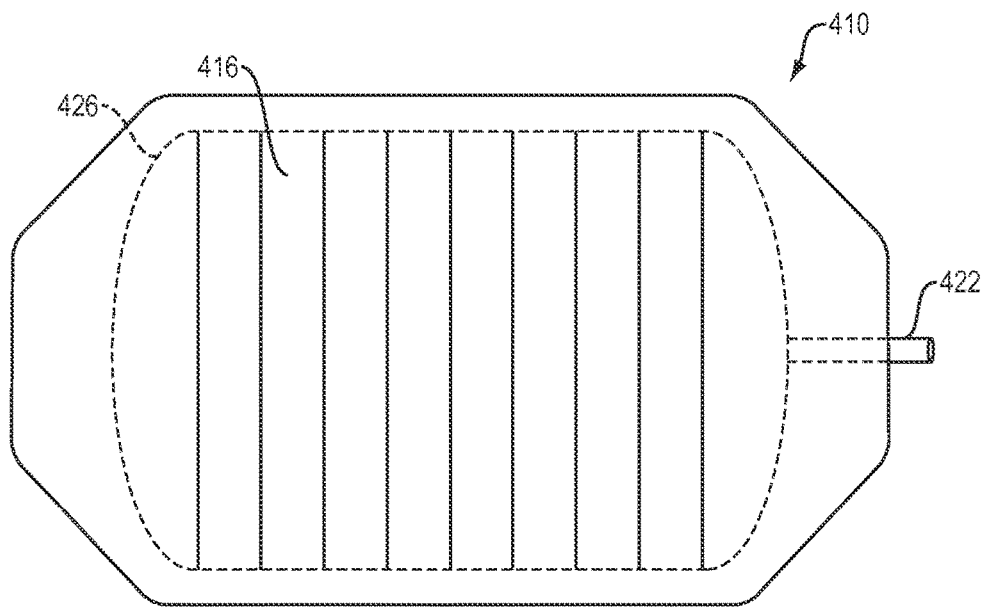
FIG. 4A is a schematic top view of another exemplary inflatable bladder in accordance with various aspects of the present teachings.
Figure 4B:
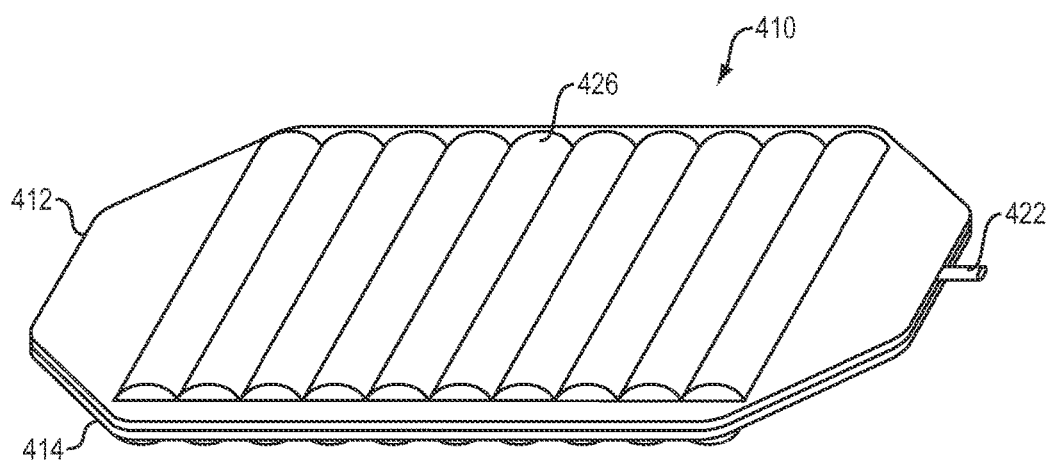
FIG. 4B is a schematic perspective of the inflatable bladder depicted in FIG. 4A when the bladder is inflated.
Figure 5A:
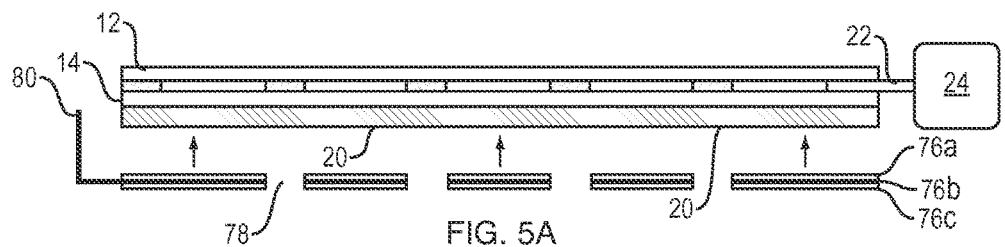
FIGS. 5A-5F are schematic diagrams depicting the harvesting of skin blisters using the exemplary skin blister harvesting device of FIG. 1.
Figure 5B:
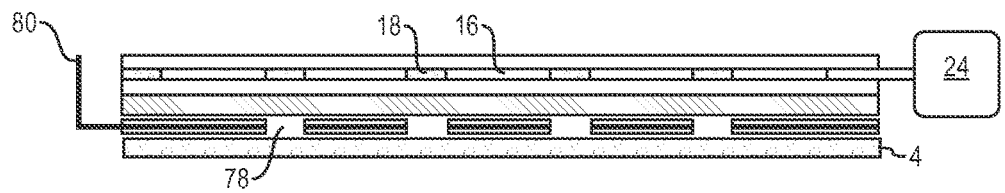
Figure 5C:
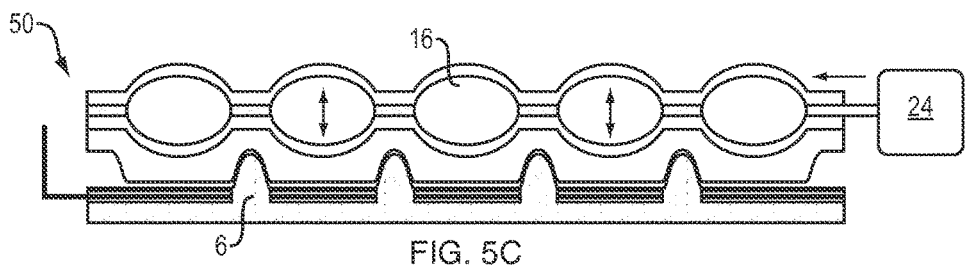
Figure 5D:
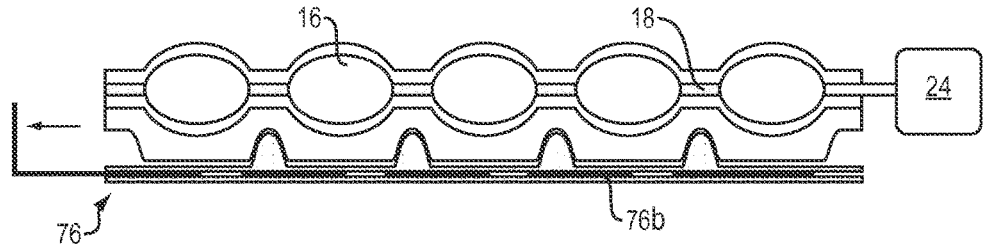
Figure 5E:
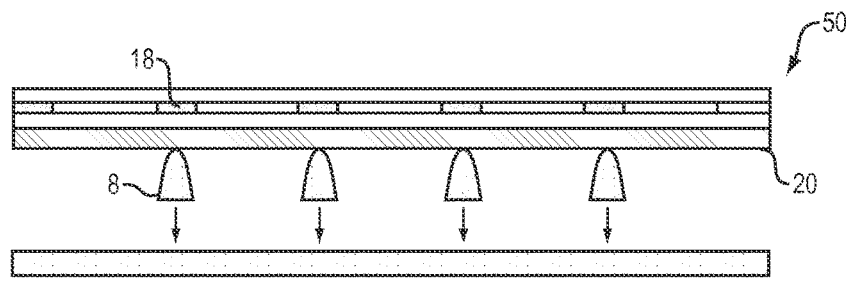
Figure 5F:

Though the exemplary bladder 10 depicted in FIGS. 1-3 comprises upper and lower layers 12, 14 that are coupled (e.g., spot welded) at a plurality of circular locations 18 that substantially correspond in a one-to-one relationship with holes 78a-c in the cutting assembly 76, it will be appreciated that inflatable bladders in accordance with the present teachings can have any number and/or configurations of non-inflatable, differentially inflatable, and/or more rigid portions so as to control the expansion of the bladder 10. For example, with reference now to FIG. 4, another exemplary bladder 410 in accordance with various aspects of the present teachings is depicted in which the upper and lower layers of the bladder 410 are coupled with one another along lines 418 that can be aligned, for example, with the pattern of holes in the cutting assembly (not shown) when the skin graft harvester is in use. For example, a single line 418 can extend over a plurality of holes in the cutting assembly and can be coupled to the skin received therein, as discussed otherwise herein. As shown in FIG. 4, as the fluid-receiving chamber 416 is inflated, the upper and lower layers 412, 414 between the lines 418 can bulge out, thereby resulting in the depicted exemplary surface contour of the bladder 410. Like the bladder 10 depicted in FIGS. 1-3 and as otherwise discussed herein, the differential expansion of the bladder 410 can be effective to selectively raise (e.g., lift) the lines 418 relative to the cutting assembly to draw portions of the skin through holes in the cutting assembly.

With reference again to FIGS. 1-3, it should be appreciated that the bladder 10 can be formed from a variety of materials that enable the expansion (e.g., shape change) described herein. By way of example, the bladder 10 can be made of a resilient or elastic material that allows for stretching of the material upon inflation of the bladder 10. As noted above, various portions of the bladder 10 can also be configured to respond (e.g., stretch, expand) differently to the filling of the chamber with a given fluid volume and/or pressure. By way of example, the bladder 10 can have selected portions that comprise more rigid materials such that a given pressure in the chamber 16 will alter the shape of the bladder 10 in a desired manner, as otherwise discussed herein. For example, while the locations 18 at which the upper and lower layers 12, 14 are depicted as being coupled to one to prevent local expansion of the bladder 10, these locations 18 could additionally or alternatively be comprised of a more rigid material (or, for example, more material of the same elasticity) relative to the surrounding areas of the bladder 10. In embodiments in which the bladder 10 comprises two layers (e.g., sheets of material coupled to one another, for example, the lower layer 14 of the bladder 10 can be of a less stiff or more elastic material relative to the upper layer 12 such that upon a given pressure applied in the chamber 16, the lower layer 14 more easily expands (e.g., changes shape). As will be discussed in detail below, such a configuration can provide for additional lift of the non-expandable portions 18 relative to the base plate 76 upon inflation of the bladder 10.

Various materials are suitable for use as the bladder 10 of the present teachings, including by way of non-limiting example, hydrophilic polyurethane; cellulosics; hydrophilic polyamides; polyvinyl alcohol; polyvinyl pyrrolidone; hydrophilic acrylics; hydrophilic silicone elastomers; an INSPIRE 2301 material from Expopack Advanced Coatings of Wrexham, United Kingdom having, for example, an MVTR (inverted cup technique) of 14400 $g/m^2/24$ hours and a thickness of about 30 microns; a thin, uncoated polymer drape; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; polyurethane (PU); EVA film; co-polyester; silicones; a silicone drape; a 3M Tegaderm® drape; a polyurethane (PU) drape such as one available from Avery Dennison Corporation of Pasadena, Calif.; polyether block polyamide copolymer (PEBAX), for example, from Arkema, France; or other appropriate material.

As will be discussed in more detail below with specific reference to FIGS. 6-10, a heat source may be associated with the skin graft harvester 50 of FIGS. 1-3 for warming the skin so as to aid in the formation of blisters. The heat source can be, by way of non-limiting example a light source (e.g., an array of incandescent lamps) or a resistive heating element (e.g., a nichrome wire) that can, for example, be placed over the bladder 10 and cutting assembly 76 depicted in FIGS. 1-3. In embodiments in which the heat source comprises a light source that emits electromagnetic radiation, for example, it may be preferable that the bladder material be clear or substantially translucent such that radiation can be transmitted therethrough in order to heat the patient's skin. In one exemplary embodiment, the bladder 10 can comprise two sheets of clear or transparent high MVTR membrane that can be sealed to one another around the periphery 26 so as to form the sealed chamber 16 therebetween, as well as at one or more additional locations (e.g., locations 18 of FIG. 2A) to control the shape change of the bladder 10 upon inflation.

As indicated above, the bladder 10 can also include a port 22 for fluidically coupling the chamber 16 to a fluid source (e.g., via one or more conduits) for filling the chamber 16 with the inflation fluid. The fluid can be a liquid (e.g., water), a gas, and a foam, all by way of non-limiting example. It will be appreciated that one or more pumps can be utilized to deliver fluid from the fluid source (e.g., reservoir) to the chamber 16 via the port 22 and/or to remove inflation fluid from the chamber 16. In some aspects, the inflation fluid can be heated so as to promote the formation of heat blisters. For example, in some aspects, the inflation fluid can be sufficiently warmed such that another heating component (e.g., light source or resistive heating element) need not be used to raise the skin blisters.

In some aspects, the lower layer of the bladder 10 can be formed from an osmotically active material such that the bladder permits the transport of water from within the chamber into the tissue with which portions of the bladder are in contact. As a result, the skin can be softened so as to facilitate blister formation. Alternatively or in addition to water both inflating the bladder 10 and diffusing across the lower layer 14 into the skin, the inner surface of the lower layer 14 (i.e., the non-skin contacting side of the lower layer 14) can be coated with a gel having a high water content (e.g., a hydrogel) so as to provide a supply of water for diffusion into the skin. Moreover, the skin-contacting surface of the lower layer 14 can additionally or alternatively include a water containing material (e.g., gel, hydrogel, hydrophilic foam, textile, or porous polymer) to be placed in contact with the skin such that water can be transported directly to the skin to aid in the formation of blisters. Exemplary gels for use in accordance with the present teachings can have a low ionic contact to promote diffusion of water into the skin. In some aspects, the gel can comprise carboxymethylcellulose (CMC) and xanthan gum gels having a high water content.

One exemplary embodiment of a cutting assembly for cleaving skin blisters formed by the skin harvester device 50 will now be described in detail with specific reference to FIGS. 1 and 2B. As noted above, the exemplary cutting assembly 76 is generally configured to be placed in contact with the skin at a donor site and disposed between the skin surface and the inflatable bladder 10. As shown in FIG. 1, the depicted exemplary cutting assembly 76 comprises a plurality of plates 76a-c, each having one or more openings 78a-c that can be initially aligned and through which portions of the skin can protrude and/or skin blisters can be formed. In the depicted embodiment, for example, the cutting assembly 76 comprises a base plate 76c configured to be disposed in contact with the skin, a top plate 76a, and a middle cutter plate 76b disposed therebetween. As noted above, each of the base plate 76c and top plate 76a can include a plurality of holes 78a,c (e.g., arranged in an array), which can be concentrically aligned, while the exemplary cutter plate 76b comprises a plurality of slots 78b that can also be initially aligned with the holes 78a,c. The cutter plate 76b, each slot 78b of which can include a cutting edge, can have an actuator coupled thereto (e.g., handle 80) for moving the cutter plate 76b relative to the base plate 78c and top plate 76a. For example, pushing or pulling on the handle 80 can move (e.g., translate, slide) the cutter plate 76b to occlude the alignment of the slots 78b with the holes 78a,c, thereby cleaving portions of the donor's skin extending through the openings 78a-c. In certain embodiments, the plates 76a-c can be coupled in their stacked configuration via one or more elastic members (e.g., springs), which can serve to keep the plates 76a-c in alignment until a lateral force is applied to one of the plates (e.g., cutter plate 76b). Upon removal of the force, the elastic members can return the plates 76a-c to their original positions such that the array of openings 78a-c in each plate 78a-c are once again aligned.

It will be appreciated that though the openings 78a,c in the top and bottom plates 76a,c are depicted as circular holes and the openings 78b in the cutter plate 76b as elongated slots, various shapes for the openings can be utilized depending, for example, on the desired shape of the micrograft. In some aspects, the openings in the cutter plate 76b can also be circular such that the holes in the cutter plate 76b can initially be concentrically aligned with the holes 78c in the base plate 76c and top plate 76a. The size of the openings in each plate can depend on the size of the graft needed, with larger holes being used in each plate to produce larger grafts. In certain embodiments, the holes range between 1 mm and 12 mm in diameter, or any specific value in between. In certain embodiments, the holes in the plates can vary in size and/or shape. For example, the holes 78a of the top plate 76a can be larger than those of the base plate 76c to facilitate blister formation and/or growth of the blister, as otherwise discussed herein.

It will be appreciated that the cutting assembly can have a variety of configurations and can be formed from a variety of materials. In some aspects, the cutting assembly 76 and components thereof can be sufficiently flexible such that the cutting assembly 76 can conform to the patient's skin at donor sites having a small radius of curvature, for example. By way of example, the plates 76a-c of the cutting assembly 76 can comprise thin, metallic plates that can conform (e.g., bend, flex) when compressed against the skin. By way of example, one or more of the plates 76a-c can comprise a perforated metal film. In some aspects, one or more of the plates 76a-c can comprise a woven metal mesh. By way of example, the top plate 76a can be a woven metal mesh that can be effective to reduce the overall rigidity of the cutting assembly 76.

It will be also be appreciated that the various features of the cutting plate can be formed, for example, lithographically by depositing a resist and patterning it (e.g., by exposure to light) such that portions of an initial plate blank are protected from etching while other portions can be removed by etching (e.g., to form the openings 78a-c). The resist can also be patterned to provide a limited amount of protection to the cutting edge portions, thereby shaping them to have less thickness (e.g., like a knife edge). The sharpness of the cutting edges can be further enhanced by electro-polishing, which will reduce the overall thickness of the cutting plate.

As indicated above, in the exemplary skin harvester device 50 depicted in FIGS. 1-3, the cutting assembly 76 is generally configured to be disposed between a surface of the patient's skin (e.g., at a donor site) and the inflatable bladder 10. In accordance with various aspects of the present teachings, the inflatable bladder 10 can be coupled to the cutting assembly 76 and/or portions of the patient's skin received within the holes 78c of the base plate 76c such that inflation of the bladder 10 is effective to raise portions of the patient's skin through the holes 78 in the cutting assembly 76. In the exemplary embodiment depicted in FIGS. 1-3, and as best shown in FIGS. 2A and 2B, the inflatable bladder 10 can be coupled to the cutting assembly 76 such that locations 18 of the upper and lower layers 12, 14 of the bladder 10 that are coupled to one another (or portions that are rigid, non-inflatable, or differentially inflatable) are aligned with the aligned holes 78 of the cutting assembly 76. For example, the coupled locations 18 of the bladder 10 can be disposed in a pattern that substantially matches the pattern of holes 78c formed in the base plate 76c, and the bladder 10 can be coupled to the cutting assembly such that the pattern of coupled locations 18 is registered with the openings 78a-c in the cutting assembly 76.

The coupling of the inflatable bladder 10 and the cutting assembly 76 and/or the portions of the skin received within the openings 78a-c in the cutting assembly 76 can be accomplished using a variety of mechanisms. By way of example, an adhesive 20 can be disposed between the inflatable bladder 10 and the cutting assembly 76 to enable removable coupling therebetween. Though the adhesive 20 is depicted in FIGS. 2B and 2C as being disposed substantially between the entire upper surface of the top plate 76a and lower layer 14 of the bladder 10, it will be appreciated in light of the present teachings that the adhesive 20 may be a continuous or a discontinuous layer of adhesive material disposed on the lower layer of the bladder 10, and that the cutting assembly 76 and bladder 10 can be coupled to one another in other ways that enables portions of the bladder 10 and/or the skin coupled thereto to move relative to the base plate 76c. By way of example, the adhesive 20 can be selectively disposed on the rigid or non-inflatable portions (e.g., locations 18) such that these locations 18 adhere to the patient's skin through the holes 78a-c in the cutting assembly 76, while the bladder 10 is coupled to the cutting assembly 76 (e.g., via top plate 76a) using a different coupling mechanism. For example, adhesives of different strengths can be applied to distinct areas to more easily enable the cutting assembly 76 to be removed (e.g., peeled) from the bladder 10 following the cleaving of the skin blisters, as discussed below. Alternatively, for example, the lower layer 14 of the bladder 10 can be maintained in contact with the cutting assembly 76 via an expandable housing or resilient couplings (e.g., springs) disposed around the perimeter of the bladder 10 that nonetheless allows for expansion of the bladder 10 such that the portions of the bladder 10 having skin coupled thereto to move relative to the base plate 76c.

It will be appreciated that any number of adhesives can be used in accordance with the present teachings in order to couple the bladder 10 to the patient's skin and/or the cutting assembly 76. For example, the adhesive 20 used to adhere the bladder 10 to a patient's skin at the donor site (and/or capture skin grafts as discussed below) and, in some aspects, to adhere the bladder 10 to the cutting assembly may be any medically-acceptable adhesive. For example, the adhesive 20 may comprise an acrylic adhesive, rubber adhesive, high-tack silicone adhesive, polyurethane, or other adhesive substance. In some embodiments, the adhesive 20 may be a pressure-sensitive adhesive comprising an acrylic adhesive with a coating weight of 15 grams/m$^2$ (gsm) to 70 grams/m$^2$ (gsm). Factors that may be utilized to control the adhesion strength may include the distribution (e.g., spacing of the adhesive 20), the thickness and amount of the adhesive 20, and the tackiness of the adhesive 20. For example, an increase in the amount of the adhesive 20 applied to portions of the bladder 10 and/or the cutting assembly 76 can generally correspond to an increase in the adhesion strength. Thus, the size and configuration of the adhesive coated portions of the bladder 10, and the amount and tackiness of the adhesive utilized may be varied to provide a desired adhesion strength between the bladder 10 and the patient's skin and/or the cutting assembly 76. As noted above and discussed otherwise herein, the adhesive can be disposed across the entire lower surface of the bladder 10 or selectively disposed on the rigid or non-inflatable portions (e.g., locations 18) such that these portions remain adhered to the patient's skin through the holes 78 in the cutting assembly 76 throughout inflation, as will be discussed below. Moreover, adhesives of different strengths can be applied to these different areas such that the adhesion strength differs across the surface of the bladder 10. In some aspects, a coating can be applied to the surfaces of the bladder 10 and/or cutting assembly 76 configured to be in contact with the adhesive so as to alter the adhesion strength between various portions. For example, an upper surface of the top plate 76a can have a coating that enables the cutting assembly 76 to more easily disengage from the bladder 10 after the skin grafts are obtained. By way of non-limiting example, the upper surface of the top plate 76a can be coated with polytetrafluoroethylene (PTFE) to ensure an easy release.

In some aspects, the adhesive can be reversible, switchable, or adjustable so as to control the adhesion strength of the components. By way of example, in some aspects, the adhesive can comprise a UV- or heat-reversible adhesive that can initially provide a high adhesion strength to aid in drawing the skin through the holes of the cutting assembly, as otherwise discussed herein, but can be deactivated when such adhesive strength is no longer desired. By way of example, as will be discussed below, after placing the skin grafts at the recipient site, the adhesive coupling the skin grafts to the bladder 10 can be deactivated such that the grafts are released. Without being limited to any particular theory, the application of UV light or thermal energy to the adhesive may increase cross-linking in the adhesive, thereby making the adhesive more brittle (and easier to disengage from the skin blisters). Alternatively, a solvent can be applied, for example, to degrade or deactivate the adhesive.

An exemplary use of the exemplary skin graft harvester depicted in FIGS. 1-3 to harvest skin grafts will now be discussed with reference to FIG. 5. As shown in FIG. 5(*a*), the inflatable bladder 10 and the cutting assembly 76 with an adhesive 20 disposed therebetween can be aligned with one another such that the holes 78 in the cutting assembly 76 are registered with more rigid or non-inflatable portions of the inflatable bladder 10 (e.g., locations 18). As shown in FIG. 5(*b*), the skin graft harvester 50 can then be placed on a donor site such that the base plate 76*c* is in contact with the surface of the skin 4. Moreover, the skin graft harvester 50 can be compressed against the skin 4 (including areas of the skin having non-flat surfaces) such that the lower layer 14 of the bladder 10 (e.g., having adhesive 20 disposed thereon) can contact portions of the skin 4 extending through the aligned holes 78 in the cutting assembly 76, and such that the adhesive 20 can bond these portions of the skin to the lower layer 14. Specifically, because of the alignment of the bladder 10 and holes 78 as described with reference to FIG. 5(*a*), the portions of the skin 4 extending through the holes 78 can be coupled to the more rigid or non-inflatable portions of the lower layer 14 (e.g., locations 18). Though FIGS. 5(*a*) and 5(*b*) depict the coupling of the cutting assembly 76 to the bladder 10 prior to disposing the skin graft harvester 50 on the skin 4, it will be appreciated that the cutting assembly 76 can instead be secured to the skin 4 prior to coupling the inflatable bladder 10 onto the cutting assembly 76.

With reference now to FIG. 5(*c*), the chamber 16 of the bladder 10 can be fluidly coupled to a fluid source and pump 24 via port 22 such that fluid can be delivered to the chamber 16 to inflate the bladder 10. It will be appreciated that the fluid source and pump 24 can generally comprise any fluid source (e.g., reservoir) or pump mechanism known in the art and modified in accordance with the present teachings. As shown in FIG. 5(*c*), as the fluid is delivered to the chamber 16, the upper and lower layers 12, 14 can expand (e.g., stretch or become taught) to accommodate the volume and/or pressure of the fluid within the chamber 16. As the bladder 10 is inflated and the portions of the bladder 10 in contact with the cutting assembly 76 expand, the bladder 10 can thus generally expand upward through the abutment of the expanding lower layer 14 against the top plate 76*a*. As a result of the upward expansion of the bladder 10, the more rigid or non-inflatable portions of the lower layer 14 (e.g., locations 18) having skin coupled thereto (e.g., via adhesive 20) are raised relative to the base plate 76*c* (e.g., hydraulically actuated) such that the skin 4 is drawn through the holes 78 in the cutting assembly 76. That is, though a maximum thickness of the bladder 10 is increased, the thickness of the bladder 10 at the coupled locations 18 remains substantially unchanged such that the coupled locations 18 are raised from the cutting assembly 76. As discussed above, the bladder 10 can be configured to generate additional lift in the locations 18 relative to the base plate 76*c* by having the expandable portions of the lower layer 14 comprise additional or different (e.g., less stiff) material relative to the top layer 12 such that the bladder 10 tends to move upward when inflated with a given volume or pressure of fluid. It will further be appreciated by those skilled in the art in light of the present teachings, that the step of inflating the bladder 10 as shown in FIG. 5(*c*) can be performed simultaneous to and/or following the application of heat to raise skin blisters 6 (e.g., through the cutting assembly 76), as generally known in the art and as otherwise discussed herein. Additionally or alternatively, the fluid delivered to the bladder 10 can comprise a heated fluid that can be effective to warm the skin 4 so as to aid in the formation of the skin blisters 6.

The bladder 10 can be maintained at a selected volume or pressure through the blister raising process until sufficient blisters 6 are raised for harvesting. In some aspects, the bladder 10 can be slowly inflated while the blisters 6 are being raised, for example, to promote the continued extension of the skin 4 through the holes 78 in the cutting assembly 76. As will be appreciated in light of the current teachings, the duration of inflation of the bladder 10, the amount of lift applied, and/or the depth of the holes 78 in the plates (i.e., the plate thickness) can determine the amount of skin 4 that extends through the holes 78, and ultimately, what type of graft will be harvested (e.g., epidermal graft, split thickness graft, or full thickness graft).

Progress of the formation of skin blisters 6 can be monitored such that when the blisters 6 have been satisfactorily formed through the aligned holes 78 in the cutting assembly 76, the skin blisters 6 can be cleaved from the skin. For example, as shown in FIG. 5(*d*), the blisters 6 can be cleaved by actuating the handle 80 such that the cutter plate 76*b* is translated or slid relative to base plate 76*c* and top plate 76*a*. As a result, alignment of holes 78 in the cutting assembly 76 through which the skin blisters 6 extend is disrupted, thereby cleaving the blisters 6 from the skin.

The bladder 10 can then be deflated and the blister harvester 50 removed from the skin surface, with the cleaved blisters 8 remaining adhered to the bladder 10, as shown in FIG. 5(*e*). Further, the cutting assembly 76, which can be removably coupled with the bladder 10 as otherwise discussed herein, can be removed from the bladder 10, while leaving the cleaved blisters 8 coupled to the lower layer 14. For example, the cutting assembly 76, which can be adhered to the bladder 10, can be peeled from the bladder 10, thus positioning the cleaved blisters 8 ready for transplantation to a recipient site 2.

The bladder 10, having the plurality of cleaved blisters 8 (i.e., skin grafts) coupled thereto, can then be placed over the area to be treated so as to form a dressing, and can be fixed in place over the treatment area, e.g., using tape or the like. The bladder 10 can be removed after sufficient time has elapsed to allow attachment and growth of the skin grafts in the treatment area, e.g., several days to a few weeks. Moreover, in some aspects, the detachment of the skin grafts from the surface of the bladder 10 can be accomplished, for example, by deactivating the adhesive 20. For example, as discussed above, the adhesive 20 for coupling the bladder 10 to the skin 4 and/or the cutting assembly 76 can be a reversible adhesive (e.g., UV or heat reversible adhesive). As such, after the skin grafts have been delivered to the recipient site 2 by the bladder 10, UV radiation, heat or a suitable solvent can be applied to the bladder 10 to release the skin grafts therefrom.

Thus, as shown in FIGS. 5(*e*) and (*f*), in some aspects the bladder 10 may not only serve to aid in blister formation, but may also obviate the need for a separate adhesive substrate (e.g., Tegaderm™) to be coupled to the blisters after harvesting for transferring the cleaved blisters from the harvesting device to the recipient site, as is commonly done in prior skin blister harvesting techniques.

With reference now to FIGS. 6-10, another exemplary embodiment of a skin graft harvester in accordance with the present teachings is depicted in which an inflatable bladder can be disposed within a housing, for example, between a head portion that can be removably coupled to a harvester body positioned at the donor site of a subject's skin. As will be described in detail below, the head portion and the body portion can define a sealed compartment that allows for the application of negative pressure to the skin (though the present teachings can in some aspects enable the harvesting of skin blisters without requiring a gas-tight seal to be formed with the skin surface, as noted above).

Figure 6:
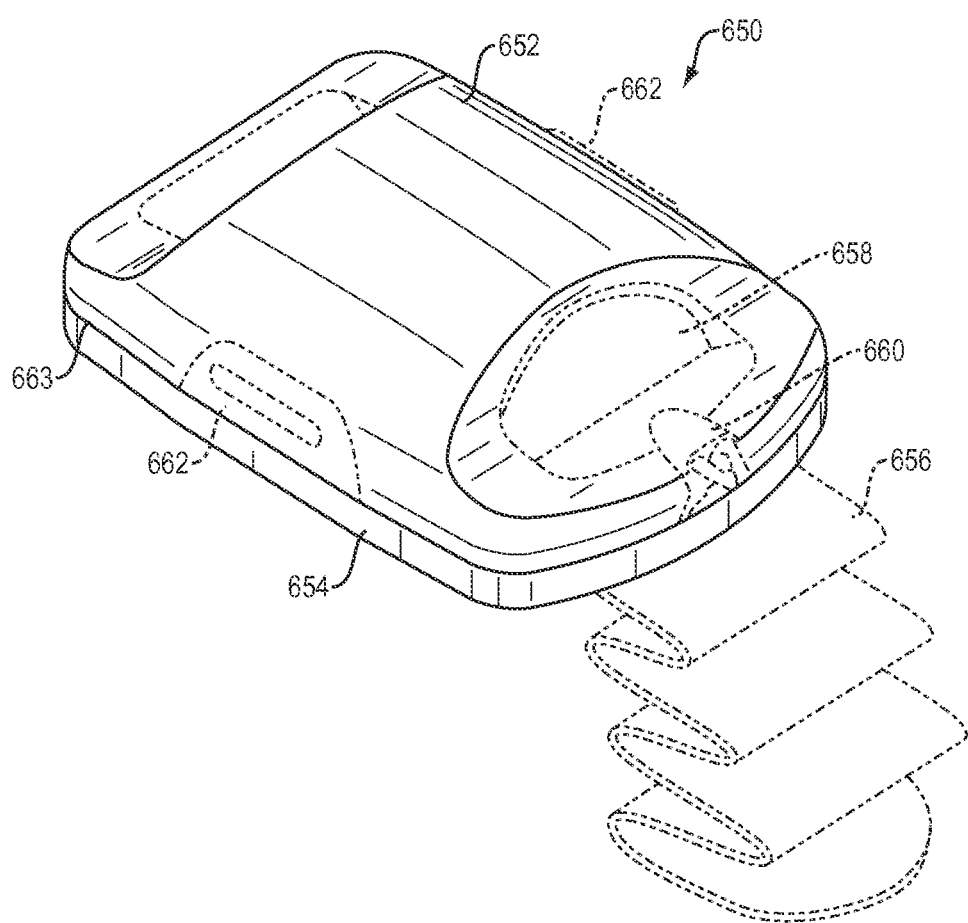
FIG. 6 is a schematic perspective of another exemplary embodiment of a skin harvesting device according to various aspects of the present teachings.

As shown in FIG. 6, the exemplary harvester 650 includes a detachable head portion 652 and a harvester body 654, which can contain a blister cutting assembly 676 and an inflatable bladder 610 in accordance with the present teachings. The harvester body 654 can be adapted for placement on a patient's skin at a donor site where skin grafts are to be obtained (e.g., on the inner thigh), and can be secured in place so as to form a seal against the skin surface, for example, with strap 656 (shown in phantom). The head portion 652 also includes a sealing surface or seal 663 such that when the head 652 and body 654 are joined together and the harvester 650 is coupled to a vacuum pump via coupler 660, for example, a sealed compartment is defined for applying a reduced pressure the patient's skin through one or more holes in the cutting assembly 676 and/or one or more holes extending through the inflatable bladder 610, as will be discussed below.

The coupler 660 can have a variety of configurations but can generally couples the internal compartment to a source of negative pressure via one or more conduits, and in some embodiments, can couple the inner chamber of the inflatable bladder 610 to an inflation fluid source. Although shown and described as part of the head portion 652, it should be clear that the coupler 660 for fluid delivery and/or evacuation of the compartment can be part of either the head 652 or the body 654 and that the inflation fluid and negative pressure can be delivered separately via multiple couplings or via a single conduit. With specific reference now to FIG. 7A, an exemplary conduit 642 is depicted as being coupled to the coupler 660, the exemplary conduit 642 comprising a flexible polymer tube having one or more internal lumens for providing fluid communication between the chamber and one or both of an inflation fluid source (e.g., an inflation fluid reservoir) or a reduced-pressure source (not shown). The conduit 642 can be fluidly coupled to the coupler 660 in any suitable manner, such as, for example, using any one of known fluid-tight couplings (e.g., by an adhesive, solvent or non-solvent bonding, welding, mechanical interlock, interference fit, etc.). As discussed otherwise herein, after disposing the inflatable bladder 610 within the compartment (e.g., atop the cutting assembly 676) and attaching (e.g., sealing) the head 652 to the body 654, an inflation fluid source and/or vacuum source can be attached to the conduit 642 to deliver inflation fluid to the chamber 616 of the inflatable bladder 610 and/or to generate negative pressure within the sealed compartment.

It will be appreciated that the reduced-pressure source can be any suitable device for providing reduced pressure effective to evacuate the compartment to aid in the formation of suction blisters such as, for example, a vacuum pump, wall suction, or other source. Although the terms "vacuum" and "negative pressure" may also be used to describe the pressure applied to the compartment, the actual pressure applied may be more than the pressure normally associated with a complete vacuum. As used herein, "reduced pressure" generally refers to a pressure less than the ambient pressure at a tissue site being subjected to treatment. Typically, this reduced pressure will be less than the atmospheric pressure. The reduced pressure may also be less than a hydrostatic pressure at a tissue site. Consistent with the use herein, an increase in reduced pressure or vacuum pressure typically refers to a relative reduction in absolute pressure. Thus, an increase in reduced pressure corresponds to a reduction in pressure (more negative relative to ambient pressure) and a decrease in reduced pressure corresponds to an increase in pressure (less negative relative to ambient pressure). Unless otherwise indicated, values of pressure stated herein are gauge pressures. While the amount and nature of reduced pressure applied to a tissue site will typically vary according to the application, the reduced pressure will typically be between −5 mmHg and −500 mmHg, and more typically in a therapeutic range between −100 mmHg and −200 mmHg. It will also be appreciated that the reduced pressure delivered may be constant or varied (e.g., patterned or random) and may be delivered continuously or intermittently.

Additional details on reduced pressure sources can be found, for example, in U.S. patent application Ser. No. 11/646,918 filed Dec. 28, 2006; U.S. patent application Ser. No. 11/810,027 filed Jun. 4, 2007; U.S. patent application Ser. No. 12/661,293 filed Mar. 15, 2010; and U.S. patent application Ser. No. 13/052,873 filed Mar. 21, 2011. The disclosures of each of these patent applications are incorporated by reference in their entireties.

In various aspects, the head portion 652 or harvester body 654 can also include one or more additional features to facilitate the harvesting of skin grafts in accordance with the present teachings. By way of example, the exemplary head portion 652 can include inter alia coupling elements for securely engaging the head portion 652 to the harvester body 654, a blister raising mechanism (e.g., via application of reduced pressure, heat, or both), and one or more windows 658 for observation of skin blisters being formed within the compartment.

Figure 7A:
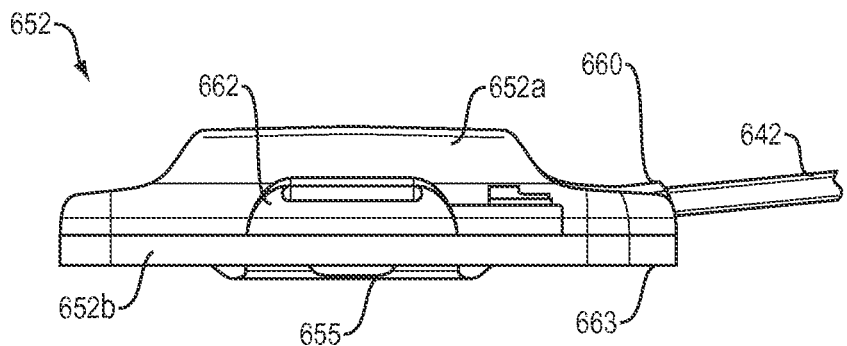
FIG. 7A is a schematic side view of a removable head portion of the skin blister harvesting device shown in FIG. 6.

For example, as shown in FIG. 7A, the exemplary head portion 652 includes a topmost, proximal portion 652a and a distal portion 652b that is configured to securely engage to the harvester body 654 so as to define a sealed chamber between the head portion 652 and the harvester body 654. Additionally, a sealing member 663 can be disposed between the head portion 652 and the harvester body 654 such that the compartment can be evacuated by the reduced pressure source with limited leakage. It will also be appreciated by a person skilled in the art that the detachable mating of the head portion 652 and harvester body 654 can be accomplished in a variety of ways. By way of example, the head 652 can include one or more mating features for engaging a corresponding mating feature of the harvester body 654. Additionally, in some aspects, the head portion 652 can include one or more release levers 662 that enable the seal to be broken, for example, after the source of reduced pressure has been deactivated, such that the head 652 can be disengaged (e.g., lifted off) the harvester body 654.

As shown in FIG. 7A, the head portion 652 can additionally include a heating component 655 for warming the skin so as to aid in the formation of skin blisters. The heating component 655, which can be by way of non-limiting example a light source (e.g., an array of incandescent lamps) or a resistive heating element (e.g., a nichrome wire) disposed within the head portion 652, can be powered via a coupler 660 to a power source in a base unit (not shown). The heat generated by the heating component 655 can be controlled, for example, by cycling the heating component 655 as needed to maintain a desired temperature within the compartment. In some aspects, the heating component 655 can be capable of emitting heat ranging between about 100° C. to about 750° C. (e.g., about 500° C.).

In some embodiments, for example, for those in which the heating component 655 comprises a light source that emits electromagnetic radiation, the distal portion 652b of the head 652 can include a transparent or a translucent surface that facilitates the transmission of electromagnetic radiation emitted from the heating element 655 to the patient's skin through the cutting mechanism 676 and/or inflatable bladder 610 and/or disposed within the compartment.

Figure 7B:
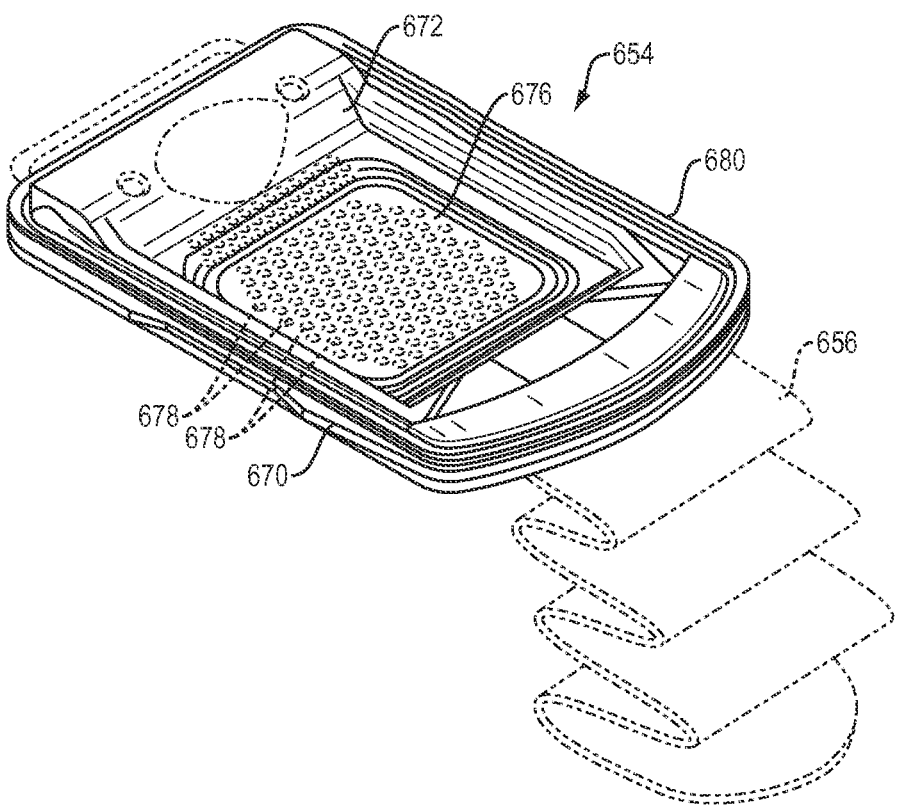
FIG. 7B is a schematic perspective of a base portion of the skin blister harvesting device shown in FIG. 6.

With reference now to FIG. 7B, the exemplary harvester body 654 of the skin graft harvester 650 of FIG. 6 with the head portion 652 removed and the cutting assembly 676 exposed is depicted. As shown in FIG. 7B, the harvester body 654 can include a base portion 670, a sled 672, and an actuator handle 680. The cutting assembly 676 includes a plurality of plates, each having a plurality of holes 678 that can be initially aligned and through which skin blisters can be drawn. Once the blisters are sufficiently formed, they can be cleaved by the cutting assembly 676. As will be discussed in detail with reference to FIG. 8, by actuation (e.g., pulling up) of handle 680, the sled 672 can be caused to move horizontally such that one of the plates below the top plate 676a moves relative to the top plate 676a (because of its linkage to the sled 672), thereby occluding the alignment of holes 678 and cleaving the raised blisters from the donor's skin.

Figure 8:
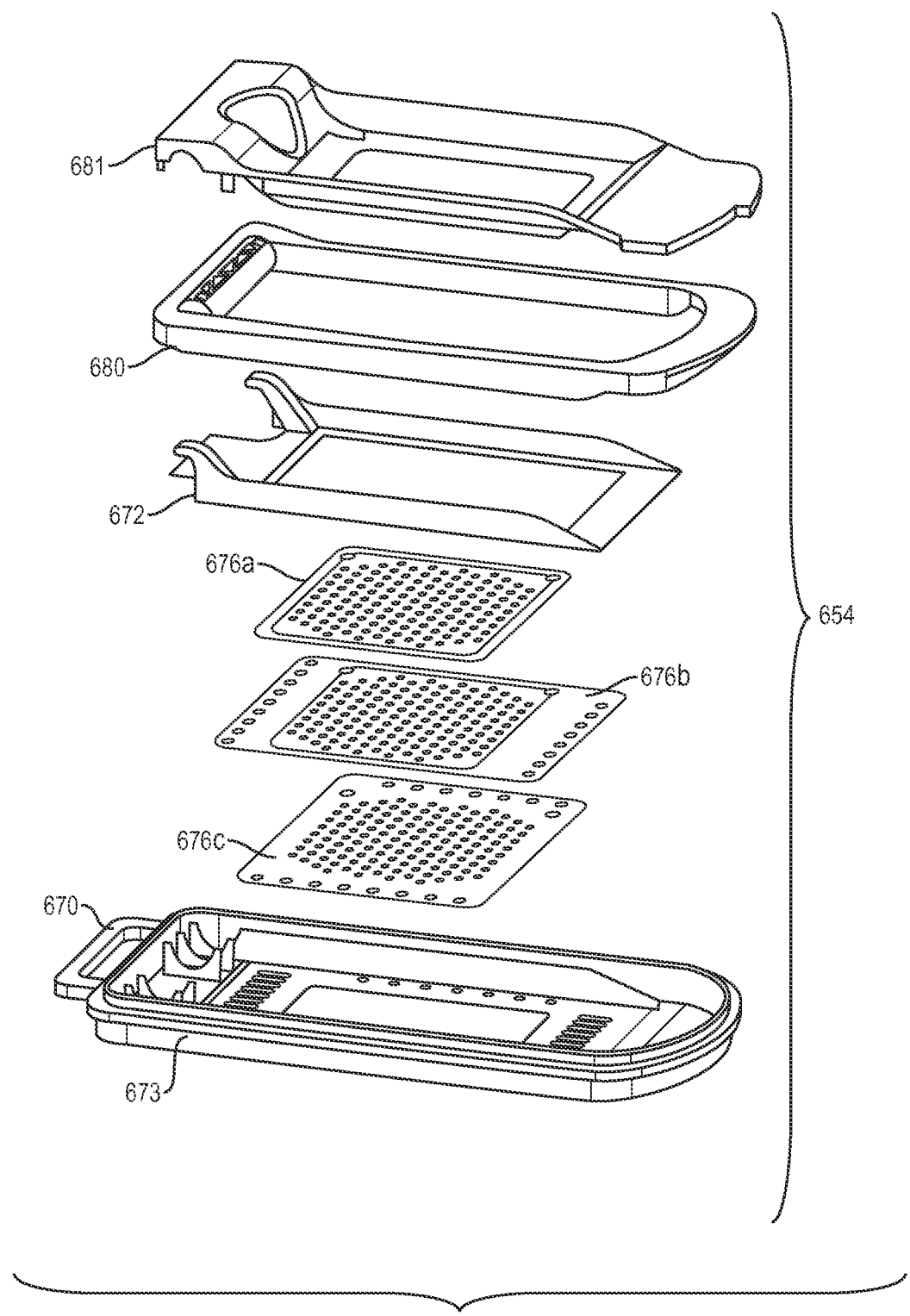
FIG. 8 is a schematic exploded view of the harvester base portion shown in FIG. 6.

FIG. 8 is an exploded view of the harvester body 654 of FIG. 7B. As shown in FIG. 8, the exemplary harvester body 654 includes a base portion 670 within which the cutting assembly 676 and actuator assembly can be disposed and a top element 681. The distal surface of the base portion 670 can include a sealing member 673 that surrounds the donor site when the harvester 650 is coupled to the patient's skin. The sealing member 673 can be formed from any material that allows for a fluid seal to prevent leakage of gas into the reduced pressure compartment. The sealing member 673 can comprise, for example, a flexible, biocompatible material. Optionally, the base portion 670 can include a strap coupler 656a to facilitate attachment of the harvester body 654 to a patient's skin.

As shown in FIG. 8, the cutting assembly 676 comprises a top and a bottom guide plate 676a,c and a middle cutter plate 676b disposed therebetween, each plate 676a-c having a plurality of holes 678 which can initially be concentrically aligned and through which blisters can be raised. For example, when the plates 676a-c are aligned and negative pressure is applied to the compartment, blisters can be formed and protrude through the aligned holes 678 in all three plates 676a-c.

The cutter plate 676b can be coupled to the sled 672 so as to move in a direction parallel to guide plates 676a,c upon actuation of the handle 680. By way of example, the cutter plate 676b can be coupled to the sled 672 in a configuration that translates the rotational movement of the handle 680 into lateral movement of the cutter plate 676b, thereby cutting the blisters that protrude through the holes 678.

Additional details on harvesters useful in connection with the present invention can be found in U.S. patent application Ser. No. 13/839,518 filed Mar. 15, 2013; U.S. patent application Ser. No. 13/346,329 filed Jan. 9, 2012; U.S. patent application Ser. No. 13/436,318 also filed Jan. 9, 2012; U.S. patent application Ser. No. 13/014,737 filed Jan. 27, 2011; U.S. patent application Ser. No. 12/851,656 filed Aug. 6, 2010; U.S. patent application Ser. No. 12/851,621 filed Aug. 6, 2010; U.S. patent application Ser. No. 12/851,703 filed Aug. 6, 2010; and U.S. patent application Ser. No. 12/851,682 filed Aug. 6, 2010. The contents of each of the above-referenced related applications are herein incorporated by reference in their entireties.

Figure 9:
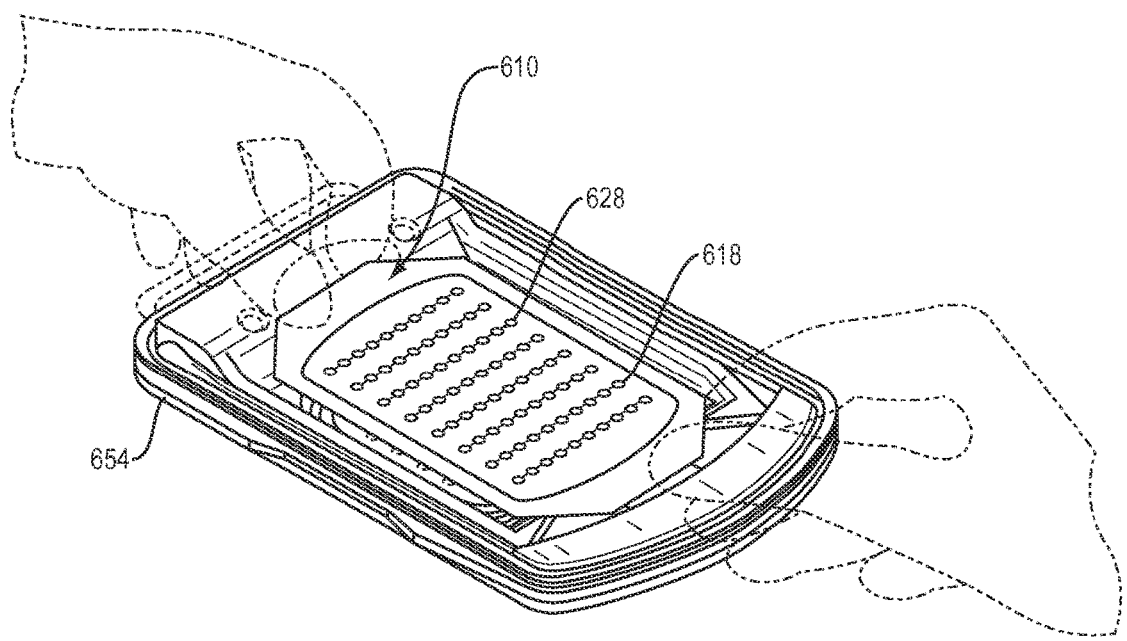
FIG. 9 is a schematic perspective of a base portion of the skin blister harvesting device shown in FIG. 6, having an exemplary inflatable bladder applied thereto.

With reference now to FIG. 9, the exemplary skin graft harvester 650 is depicted prior to coupling of the head 652 with the harvester body 654. As shown in FIG. 9, an inflatable bladder 610 can be disposed within the harvester body 654 atop the cutting assembly 676 and can be coupled thereto as otherwise discussed herein (e.g., via an adhesive). Rather than disposing the adhesive continuously across the entire lower surface of the bladder 610, in some aspects the head 652 can maintain inflatable portions of the bladder 610 in contact with the cutting assembly 676 when the head 652 is sealed to the harvester body 654 (e.g., via one or more features formed on an inner surface of the harvester body 652), while nonetheless allowing portions of the bladder 10 having skin coupled thereto (e.g., via an adhesive selectively disposed on skin contacting locations of the bladder) to move relative to the bottom guide plate 676c. After aligning the bladder 610 with the holes 678 in the cutting assembly 676, and compressing the bladder 610 to adhere skin portions received within the holes 678 to the bladder, the head 652 and the harvester body 654 can be sealed.

Figure 10A:
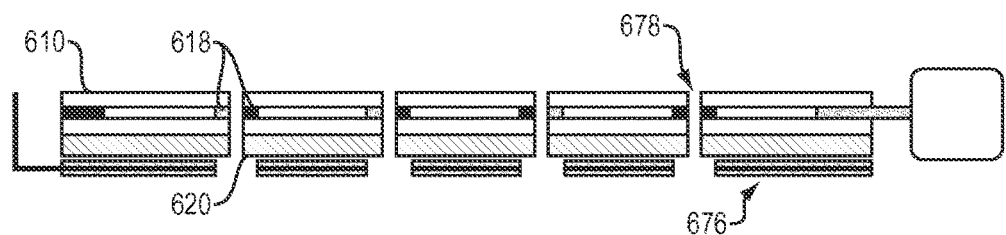
FIG. 10A is a schematic cross-sectional view of the inflatable bladder of FIG. 9 when the bladder is not inflated.
Figure 10B:
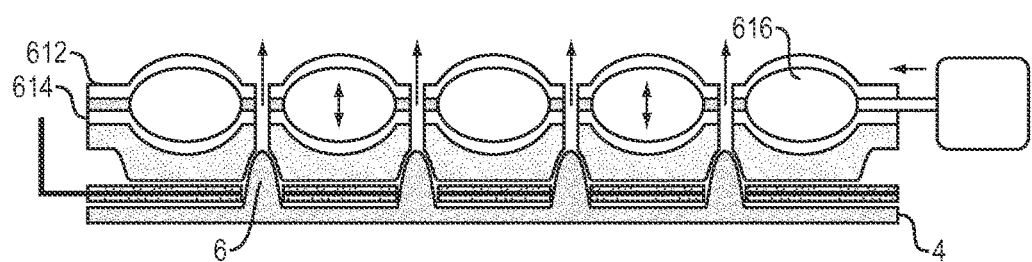
FIG. 10B is a schematic cross-sectional view of the inflatable bladder of FIG. 9 when the bladder is inflated.

With reference now to FIGS. 9 and 10, the exemplary inflatable bladder 610 for use in the skin graft harvester 650 is described in more detail. The inflatable bladder 610 is substantially similar to the inflatable bladder 10 described above with reference to FIGS. 1-5, but differs in that the inflatable bladder 610 includes channels extending therethrough to enable the bladder 610 to utilize the negative pressure generated in the compartment for suction blistering to aid in coupling the bladder 610 to the skin. By way of example, the exemplary inflatable bladder 610 can comprise an upper layer 12 and a lower layer 14 that can be coupled to one another in various locations such that the bladder 610 differentially expands upon inflation. As best shown in FIG. 9, for example, the upper and lower layers of the bladder 410 can be coupled with one another along lines 618 that can be aligned, for example, with the pattern of holes 678 in the cutting assembly 676 when the bladder is disposed within the harvester body 654. As described above with reference to FIG. 4, for example, a single line 618 can extend over a plurality of holes 678 in the cutting assembly 676 and can be coupled to the skin received therein. The exemplary bladder 610 additionally includes one or more channels 628 that can extend between the upper surface and lower surface of the bladder through the more rigid or non-inflatable portions of the bladder (e.g., along line 618). By aligning the channels 628 with the holes 678 in the cutting assembly 676 as schematically depicted in FIG. 10A, a negative pressure generated within the sealed compartment of the skin graft harvester 650 can be applied to the skin via the channels 628 extending through the bladder 610. For example, as depicted in FIG. 10B, the bladder 610 can be inflated concurrent with the application of a negative pressure therethrough. As such, the bladder 610 can be more securely coupled to the skin 4, and can aid in extending the skin blisters 6 coupled thereto through the holes 678 in the cutting assembly 676. Moreover, as discussed above with reference to FIG. 5, upon cleaving the blisters from the skin, the bladder 610 can be removed from the skin graft harvester 650 with the skin blisters coupled thereto to allow for direct transplantation to a recipient site.

Figure 11A:
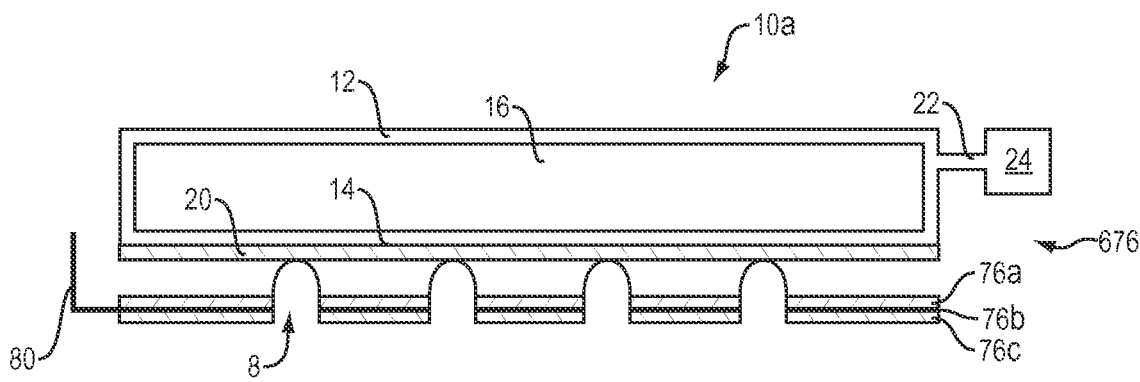
FIG. 11A is a schematic cross-sectional view of another embodiment of the inflatable bladder when the bladder is not inflated.
Figure 11B:
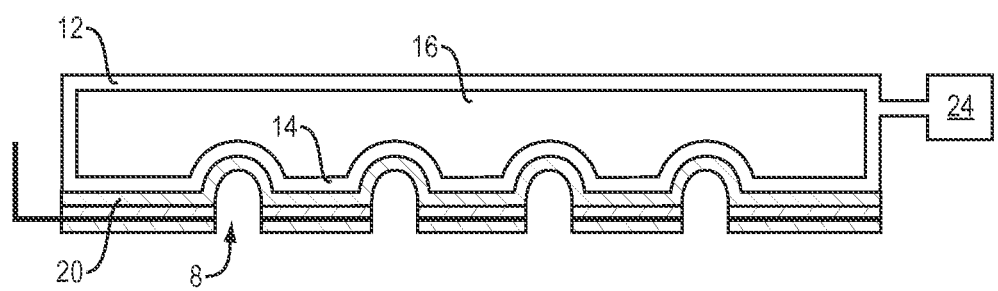
FIG. 11B is a schematic cross-sectional view of the inflatable bladder of FIG. 11A when the bladder is inflated.

In FIGS. 11A and 11B, another embodiment of a harvesting device 10A is shown in conjunction with a cutter assembly 676 (e.g., 76a, 76b, 76c and 80). The harvesting device 10A includes a rigid top layer 12 and a flexible lower layer 14, defining an inflation cavity 16 therebetween. The device 10A, preferably, is secured to a harvester body (as discussed above in conjunction with FIG. 7). Device 10A is designed to be used with an adhesive transfer substrate 20, which can be a conventional transfer substrate (such as Tegaderm, Adaptic Touch, etc.) to provide consistent and evenly distributed pressure to grafts so that they better adher to the transfer substrate prior to, or after, cutting.

As shown in FIG. 11B, when the device 10A is inflated, the cavity (bladder) 16 expands and forces the adhesive substrate into contact with the cutter assembly and the skin blisters 8 protruding therethrough. In one embodiment, grafts can be formed with existing reduced pressure skin blister systems. For example, the vacuum head can be removed following blister formation, the transfer substrate or dressing applied to the top of the grafts, the inflatable bladder placed on top of the transfer substrate with the rigid layer of the inflatable bladder secured to the harvester. The inflatable bladder can then be inflated to a known pressure, and inflate between the rigid layer and the harvester base, providing evenly distributed pressure to the transfer substrate. Then the bladder is deflated, removed from the harvester, and the cutter mechanism can be engaged to cut the grafts. The transfer dressing can then be removed with grafts. This embodiment can ensure that the adhesive is distributed to all grafts and also ensure there is no over-pressure applied to grafts, which may cause them to rupture before transfer.

Figure 12:
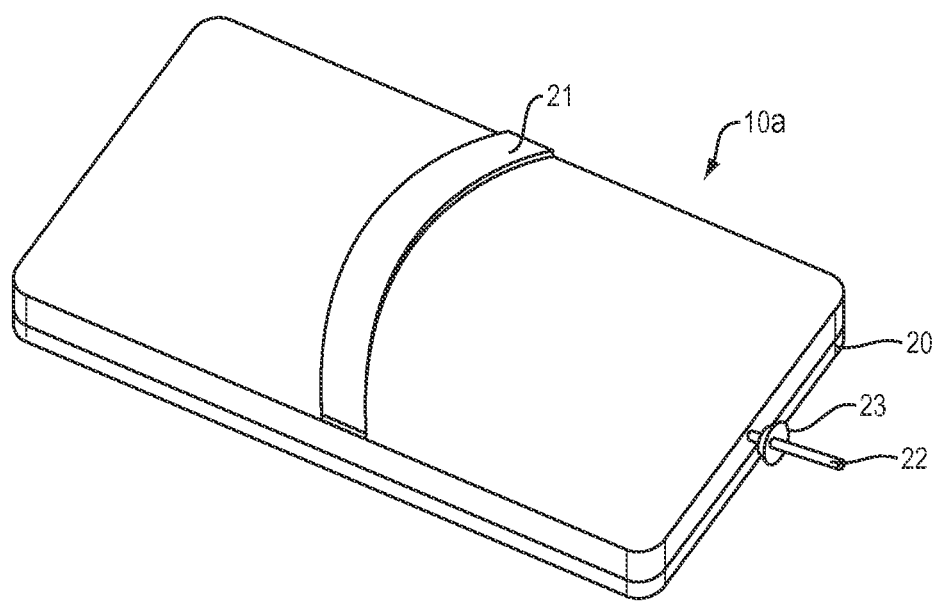
FIG. 12 is a schematic perspective view of a side graft harvesting device according to the invention with a carrying strap.

In some embodiments, as shown in FIG. 12, the harvester device 10A with adhesive substrate can be left inflated, and can further include a strap 21, such that it can be transferred directly to the wound, providing a flexible, evenly distributed bolster for grafts to maintain contact with the wound. The bladder would have a one-way valve 23 to minimize leaks, and can retain a port or conduit 22 to connect to a powered or non-powered pressure device.

With the exemplary steps described above, systems in accordance with the present teachings can be used to prepare any type of skin graft, such as an epidermal skin graft, a split thickness graft, or a full thickness graft. However, the device of the invention is particularly well suited for preparing skin grafts including only or substantially only the epidermal layer of skin. The device of the invention can be used for autografts, allografts, or xenografts for the repair of numerous different types of skin damage. For example, harvested grafts may be used to treat burns (e.g., both thermal and chemical burns), blistering, dermatological conditions (e.g., epidermolysis bullosa or pyoderma gangrenosum), radiation therapy ulcers, diabetic ulcers, ischemic ulcers, trophic ulcers, trauma, or depigmentation (e.g., vitiligo).

Certain embodiments of the exemplary devices described herein integrate consumable/single-use and re-usable, sterilizable or cleaned components, thereby providing a reliable system that is easy to maintain. All components of devices that come into contact with the donor and/or recipient tissue (both single-use and reusable components) must be sterile/sterilized to reduce the risk of infection. In some aspects, non-single use polymeric portions of the system can be manufactured with an anti-microbial material within the polymer to as to prevent the growth of bacteria therein.

References and citations to other documents, such as patents, patent applications, patent publications, journals, books, papers, web contents, have been made throughout this disclosure. All such documents are hereby incorporated herein by reference in their entirety for all purposes.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for skin graft harvesting comprising:
an inflatable bladder having an upper surface and a lower surface and defining at least one inflatable chamber between the upper and lower surfaces, the bladder configured to be disposed upon a cutting assembly having a plurality of holes through which skin grafts may be raised;
an inflation port for inflating the bladder; and
an adhesive applied to at least a portion of the lower surface of the bladder to permit exposed skin portions to adhere to the lower surface when the bladder is disposed upon the cutting assembly and the cutting assembly is applied to the skin,
wherein inflation of the bladder is effective to deform the bladder and draw adherent portions of the skin through the holes in the cutting assembly.

2. A device for obtaining a skin graft, the device comprising:
an inflatable bladder defining at least one chamber therein; and
a cutting assembly configured to be disposed between the bladder and the skin surface at a donor site, wherein the cutting assembly comprises:
a base plate having a plurality of holes for receiving portions of the skin when the base plate is disposed on the skin surface; and
a cutter plate disposed between the base plate and the bladder and configured to cleave the portions of the skin extending through said plurality of holes in said base plate,
wherein the inflatable bladder is coupled to the cutting assembly such that inflation of the bladder is effective to raise portions of the skin through said plurality of holes.

3. The device of claim 2, wherein the inflatable bladder comprises non-inflatable portions in register with the plurality of holes.

4. The device of claim 3, wherein the non-inflatable portions are configured to couple to the portions of the skin through the plurality of holes via an adhesive.

5. The device of claim 3, wherein inflation of the bladder is effective to raise the non-inflatable portions of the bladder relative to the base plate.

6. The device of claim 2 wherein the inflatable bladder further comprises an adhesive transfer substrate adapted for disposition between a lower layer of the inflatable bladder and the cutter assembly such cleaved skin grafts will adhere to the substrate.

7. The device of claim 6 wherein the bladder and transfer substrate form a transfer dressing that can be removed with the grafts to transfer the grafts to a wound.

8. The device of claim 7 wherein the transfer dressing further comprises a strap for transporting the graft.

9. A device for obtaining a skin graft, the device comprising:
an inflatable bladder having an upper layer and a lower layer defining at least one chamber therebetween; and
a cutting assembly configured to be disposed between the bladder and the skin surface at a donor site, wherein the cutting assembly comprises:
a base plate having a plurality of holes through which portions of the skin at the donor site can be coupled to the lower layer of said inflatable bladder; and
a cutter plate disposed between the base plate and the bladder and configured to cleave skin extending through said plurality of holes following blister formation.

10. The device of claim 9, wherein the inflatable bladder comprises one or more ports for fluid coupling of the at least one chamber to a fluid source.

11. The device of claim 9, wherein inflation of the bladder is effective to raise relative to the base plate at least a portion of the lower layer of the bladder having skin coupled thereto.

12. The device of claim 9, wherein inflation of the bladder is effective to pull portions of the skin coupled to the lower layer through said plurality of holes.

13. The device of claim 9, wherein said upper and lower layers of the inflatable bladder comprise a polymeric membrane.

14. The device of claim 9, wherein the upper layer comprises a stiffer polymeric material relative to the lower layer.

15. The device of claim 9, wherein locations of the upper and lower layers are coupled to one another such that a distance between said upper and lower layers at said coupled locations remains substantially constant during inflation of the bladder, and wherein a distance between said upper and lower surfaces between said coupled locations increases during inflation of the bladder.

16. The device of claim 15, wherein inflation of the bladder is effective to raise the lower layer at said coupled locations relative to the base plate.

17. The device of claim 15, wherein said at least one fluid receiving chamber extends between adjacent coupled locations of said upper and lower layers.

18. The device of claim 15, wherein said coupled locations are aligned with said plurality of holes in said base plate.

19. The device of claim 15, wherein said coupled locations comprise a channel extending through the upper and lower layers.

20. The device of claim 19, wherein said channel is configured to couple to a source of negative pressure such that application of negative pressure within said channel promotes suction blister formation.

21. The device of claim 19, wherein said channel is configured to couple to a source of negative pressure such that application of negative pressure within said channel is effective to maintain said raised portions of the skin in secure contact with said lower layer.

22. The device of claim 9, wherein the cutting assembly is removably coupled to the lower layer of said bladder.

23. The device of claim 9, wherein the cutting assembly further comprises a top plate configured to be disposed between the cutter plate and the lower layer of the inflatable bladder, the top plate defining one or more holes extending therethrough in alignment with said plurality of holes in the base plate.

24. The device of claim 23, wherein the top plate is removably coupled to the lower layer of the inflatable bladder via an adhesive.

25. The device of claim 9, further comprising an adhesive disposed on the lower layer of the bladder.

26. The device of claim 25, wherein the adhesive is configured to removably couple the lower layer of the bladder to said portions of the skin at said target area through said plurality of holes in said base plate.

27. The device of claim 25, wherein the adhesive comprises at least one of UV or heat reversible adhesive.

28. The device of claim 9, further comprising a heating element for heating the skin at the target area so as to promote blister formation through said plurality of holes.

29. The device of claim 28, wherein the heating element comprises one of a light source and a resistive heating element.

30. The device of claim 29, wherein the cutter plate has a plurality of holes extending therethrough, and wherein the cutter plate is configured to move relative to the base plate from a first position in which the plurality of holes in the base plate and the cutter plate are aligned to a second position in which the alignment is disrupted so as to cut said blisters.

31. The device of claim 9, further comprising a top plate disposed between the cutter plate and the lower layer of the bladder, the top plate having a plurality of holes in alignment with said plurality of holes in said base plate.

32. The device of claim 31, wherein the top plate is removably coupled to the lower layer.

33. The device of claim 9 wherein the inflatable bladder further comprises an adhesive transfer substrate adapted for disposition between a lower layer of the inflatable bladder and the cutter assembly such cleaved skin grafts will adhere to the substrate.

34. The device of claim 33 wherein the bladder and transfer substrate form a transfer dressing that can be removed with the grafts to transfer the grafts to a wound.

35. The device of claim 34 wherein the transfer dressing further comprises a strap for transporting the graft.

36. A system for obtaining a skin graft, the system comprising:
an inflatable bladder having an upper layer and a lower layer defining at least one chamber therebetween;
a fluid source fluidly coupled to said chamber for inflating said bladder;
a heating element for heating a donor site of a patient's skin; and
a cutting assembly configured to be disposed between the bladder and the skin surface at the donor site, wherein the cutting assembly comprises:
a base plate having a plurality of holes through which portions of the skin at the donor site can be coupled to the lower layer of said bladder; and
a cutter plate disposed between the base plate and the bladder and configured to cleave portions of the skin raised through said plurality of holes following blister formation.

37. The system of claim 36, wherein the inflatable bladder comprises one or more ports for fluid coupling of the at least one chamber to the fluid source.

38. The system of claim 36, wherein inflation of the bladder is effective to pull portions of the skin coupled to the lower layer through said plurality of holes.

39. The system of claim 36, wherein portions of the upper and lower layers are coupled to one another such that a distance between said upper and lower layers at said coupled portions remains substantially constant during inflation of the bladder, and wherein a distance between said upper and lower surfaces between said coupled portions increases during inflation of the bladder.

40. The system of claim 39, wherein said coupled portions are aligned with said plurality of holes in said base plate.

41. The system of claim 39, further comprising a source of negative pressure fluidly coupled to a channel formed through said coupled portions of the upper and lower layers.

42. The system of claim 41, wherein application of negative pressure within said channel promotes suction blister formation.

43. The system of claim 36, wherein the fluid comprises one of liquid or gas.

44. The system of claim 36, wherein the fluid comprises a heated liquid.

45. The system of claim 36, further comprising a pump for delivering fluid from the fluid source to the chamber.

46. The system of claim 36, further comprising an adhesive disposed on the lower layer of the bladder, wherein the adhesive is configured to removably couple the lower layer of the bladder to said portions of the skin at said target area through said plurality of holes in said base plate.

47. The system of claim 36 wherein the inflatable bladder further comprises an adhesive transfer substrate adapted for disposition between a lower layer of the inflatable bladder and the cutter assembly such cleaved skin grafts will adhere to the substrate.

48. The system of claim 47 wherein the bladder and transfer substrate form a transfer dressing that can be removed with the grafts to transfer the grafts to a wound.

49. The system of claim 48 wherein the transfer dressing further comprises a strap for transporting the graft.

50. A system for obtaining a skin graft, the system comprising:
an inflatable bladder defining at least one chamber therein;
a fluid source fluidly coupled to said chamber for inflating said bladder;
a heating element configured to heat a donor site of a patient's skin; and
a cutting assembly configured to be disposed between the bladder and the skin surface at the donor site, wherein the cutting assembly comprises:
a base plate having a plurality of holes for receiving portions of the skin when the base plate is disposed on the donor site; and
a cutter plate disposed between the base plate and the bladder and configured to cleave portions of the skin extending through said plurality of holes,
wherein the inflatable bladder is coupled to the cutting assembly such that inflation of the bladder is effective to raise portions of the skin through said plurality of holes.

51. The system of claim 50, wherein the inflatable bladder comprises non-inflatable portions in register with the plurality of holes.

52. The system of claim 51, wherein inflation of the bladder is effective to raise the non-inflatable portions of the bladder relative to the base plate.

53. The system of claim 50 wherein the inflatable bladder further comprises an adhesive transfer substrate adapted for disposition between a lower layer of the inflatable bladder and the cutter assembly such cleaved skin grafts will adhere to the substrate.

54. The system of claim 53 wherein the bladder and transfer substrate form a transfer dressing that can be removed with the grafts to transfer the grafts to a wound.

55. The system of claim 54 wherein the transfer dressing further comprises a strap for transporting the graft.

56. A method of generating a skin graft, the method comprising:
applying a cutting assembly to a donor site of a patient's skin, the cutting assembly comprising a base plate for contact with the skin and having a plurality of holes extending therethrough;
coupling an inflatable bladder to portions of the patient's skin at the donor site through said plurality of holes in said base plate;
inflating said bladder at least one of during and after heating said skin to thereby raise one or more blisters through said plurality of holes in said base plate; and
actuating the cutting assembly to cleave the blisters from the donor site.

57. The method of claim 56, wherein the cutting assembly comprises a cutter plate disposed between the base plate and the inflatable bladder, and wherein actuating the cutting assembly comprises moving the cutter plate relative to the base plate.

58. The method of claim 57, wherein actuating the cutter plate comprises moving the cutter plate from a first position in which a plurality of holes extending therethrough are aligned with the holes in the base plate to a second position in which the alignment of the plurality of holes in the base plate and cutter plate is disrupted.

59. The method of claim 56, further comprising coupling the cutting assembly to the inflatable bladder prior to applying the cutting assembly to the donor site.

60. The method of claim 56, wherein an adhesive is disposed on a lower layer of said inflatable bladder, and wherein the portions of the skin at the donor site are coupled to the lower layer of the bladder by compressing the base plate against the skin.

61. The method of claim 60, wherein the inflatable bladder is coupled to the cutting assembly via said adhesive.

62. The method of claim 60, wherein the adhesive comprises at least one of a UV- or heat-deactivated adhesive, wherein the method further comprises deactivating the adhesive after applying the plurality of cleaved blisters to a donor site.

63. The method of claim 56, further comprising deflating the inflatable bladder after cleaving the blisters from the donor site.

64. The method of claim 56, further comprising removing the inflatable bladder from the donor site after cleaving the blisters therefrom, the inflatable bladder having the plurality of cleaved blisters coupled thereto.

65. The method of claim 64, further comprising applying the inflatable bladder having the plurality of cleaved blisters coupled thereto to a graft site.

66. The method of claim 56, further comprising:
removing the inflatable bladder having the cutting assembly coupled thereto from the donor site; and
removing the cutting assembly from the inflatable bladder prior to applying the inflatable bladder having the plurality of cleaved blisters coupled thereto to a graft site.

67. The method of claim 56 wherein the step of coupling an inflatable bladder to portions of the patient's skin at the donor site further comprises deposing an adhesive transfer substrate between a lower layer of the inflatable bladder and the cutting assembly and inflating the bladder to deliver pressure to the transfer substrate.

68. The method of claim 67 wherein the method further comprises deflating the bladder and removing it before the cutting assembly is actuated.

69. The method of claim 68 wherein the step of actuating the cutting assembly to cleave the blisters from the donor site further comprises causing the blisters to adhere to the substrate as grafts, and then removing the transfer substrate with the grafts.

70. The method of claim 67 wherein the step of actuating the cutting assembly to cleave the blisters from the donor site further comprises causing the blisters to adhere to the substrate as grafts, and then removing the bladder and transfer substrate together as a transfer dressing.

* * * * *